United States Patent
Kleanthous et al.

(10) Patent No.: US 6,585,975 B1
(45) Date of Patent: *Jul. 1, 2003

(54) USE OF SALMONELLA VECTORS FOR VACCINATION AGAINST HELICOBACTER INFECTION

(75) Inventors: Harold Kleanthous, Westford, MA (US); Patricia Londono-Arcila, London (GB); Donna Freeman, Cambridge (GB); Cynthia K. Lee, Needham, MA (US); Thomas P. Monath, Harvard, MA (US)

(73) Assignee: Acambis, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/431,705

(22) Filed: Nov. 1, 1999

Related U.S. Application Data

(63) Continuation-in-part of application No. PCT/US98/08890, filed on Apr. 30, 1998.

(51) Int. Cl.$^7$ .............................................. A61K 39/02
(52) U.S. Cl. .................. 424/200.1; 424/234.1; 435/69.1; 435/6; 514/44; 536/23.5
(58) Field of Search .......................... 424/234.1, 200.1; 536/23.5; 514/44; 435/184, 6, 69.1

(56) References Cited

U.S. PATENT DOCUMENTS

| | | | |
|---|---|---|---|
| 4,888,170 A | | 12/1989 | Curtiss, III |
| 5,538,729 A | * | 7/1996 | Czinn et al. .............. 424/234.1 |
| 5,547,664 A | * | 8/1996 | Charles ..................... 424/93.2 |
| 5,683,700 A | | 11/1997 | Charles et al. |
| 5,783,196 A | * | 7/1998 | Noriega et al. .......... 424/234.1 |
| 5,843,426 A | * | 12/1998 | Miller et al. .............. 424/93.2 |
| 5,843,460 A | * | 12/1998 | Labigne et al. .......... 424/234.1 |
| 5,877,159 A | * | 3/1999 | Powell et al. ................ 514/44 |
| 5,888,799 A | | 3/1999 | Curtiss, III |
| 5,928,865 A | * | 7/1999 | Covacci .......................... 435/6 |
| 5,985,631 A | * | 11/1999 | Soman et al. ............... 435/184 |
| 6,005,090 A | * | 12/1999 | Doidge et al. ............. 536/23.5 |
| 6,024,961 A | | 2/2000 | Curtiss, III et al. |
| 6,030,624 A | * | 2/2000 | Russell .................... 424/200.1 |
| 6,126,938 A | * | 10/2000 | Guy et al. ................ 424/184.1 |
| 6,383,496 B1 | * | 5/2002 | Curtiss, III et al. ...... 424/200.1 |

FOREIGN PATENT DOCUMENTS

| | | | |
|---|---|---|---|
| EP | 835928 A1 | * | 4/1998 |
| WO | 9215688 | * | 9/1992 |
| WO | 9318150 | * | 9/1993 |
| WO | 9522987 | * | 8/1995 |
| WO | 9640893 | * | 12/1996 |
| WO | 9702835 | * | 1/1997 |
| WO | WO 99/21959 | | 5/1999 |

OTHER PUBLICATIONS

Goldman, B.S. et al, Asdtr. Gen. Meet. Am. Soc. Microbiol., vol. 91(0), p. 229, 1991.*
Corthesy–Theulaz et al, Vaccine Weekly, PN/A, Mar. 23, 1998, (abstract), 1998.*
Dore–Davin et al, Gastroenterology, vol. 110(4), May, p. A898 (abstract), 1996.*
Haas, R et al, Biologicals, vol. 25, pp. 175–177, 1997.*
Corthesy–Theulaz et al, Gastroenterology, vol. 112(4 suppl), p. A953, 1997.*
Corthesy–Theulaz, I.E. et al, Infection Immunity, Feb., vol. 6692), pp. 581–586, 1998.*
Hartman, AB et al, Infection Immunity, Feb., vol. 62(2), pp. 412–420, (abstract), 1994.*
Keren, DF et al, Infection Immunity, Apr., vol. 56(4), pp. 919–915, (abstract), 1988.*
Kwon, D.H. et al, Gut vol. 41(suppl 1), p. A15, 1997.*
Gomez–Durarte, OG et al, Vaccine, Mar., vol. 16(5), pp. 460–467,(abstract), 1998.*
Gomez–Durate, OG et al, Gut, vol. 41(suppl 1), p. A59–A60, (abstract), 1997.*
Lugtenburg, T. Safety and efficacy of oral or combined oral and parenteral immunization with inactivated or live avirulent bacteria against *Salmonella typhimurium* in the calf., Ludwig–Maximilians Universitat, Munchen (abstrct of thesis), 1981.*
Tacket, CO et al, Vaccine Weekley, pN/A, Mar. 17, *Salmonella typhi*"Safety of live oral *salmonella typhi* vaccine strains with deletions in htrA and aroCaroD and Immune response in Humans." (abstract), 1997.*
Tacket, C.O. et al, Infection Immunity, Feb., vol. 65(2), pp. 452–456, 1997.*
Hone, D.M. et al, J. Clin. Invest., vol. 90, pp. 412–420, 1992.*
Gonzalez, C et al, J. Infectious Diseases, vol. 169, pp. 927–931, 1994.*
Tomb, J.F et al, Nature, vol. 388, Aug., pp. 539–547, 1997.*
Torres, JF et al, Infection Immunity, vol. 63(12), pp. 4619–4627, Dec., 1995.*
Szostak, M.P. et al, Behring Inst. Mitt, No. 98, pp. 191–196, 1997.*
Chen, M et al, Gastroenterology, vol. 104(4), Apr., p. A681, 1993.*
Anderson et al., "Delivery of the Pertactin/P.69 Polypeptide of *Bordetella pertussis* Using an Attenuated *Salmonella typhimurium* Vaccine Strain: Expression Levels and Immune Response," Vaccine 14:1384–1390 (1996).

(List continued on next page.)

Primary Examiner—Lynette R. F. Smith
Assistant Examiner—Ginny Allen Portner
(74) Attorney, Agent, or Firm—Clark & Elbing LLP

(57) ABSTRACT

The invention provides a method of immunization against Helicobacter, involving mucosal administration of an attenuated Salmonella vector including a nucleic acid molecule encoding a Helicobacter antigen, and parenteral administration of a soluble Helicobacter antigen, co-administered with a suitable parenteral adjuvant. Also provided by the invention are attenuated Salmonella vectors for use in this method.

15 Claims, 8 Drawing Sheets

OTHER PUBLICATIONS

Ward et al., "Immunogenicity of a *Salmonella typhimurium aroA aroD* Vaccine Expressing a Nontoxic Domain of *Clostridium difficile* Toxin A," Infection and Immunity 67:2145–2152 (1999).

Lee et al., "Immunization of Rhesus Monkeys with Mucosal Prime, Parenteral Boost Strategy Protects against Infection with *Helicobacter pylori*," Abstract–Vaccine 17:3072–3082 (1999).

Fulginiti, J et al , Oral immunization of mice with live attenuated S.typhimurium expressing H.pylori urease, Abstracts of papers presented at the meeting on Molecular approasches to the control of Infectious diseases, 1995, p. 27, Cold Spring Harbor.*

Krachenbuhl, JP, Infectious Disease Weekly, pN/A, Jul. 8, 1996, Vaccine Development "Vaccines of Tomorrow: The Hope of Science."*

* cited by examiner-

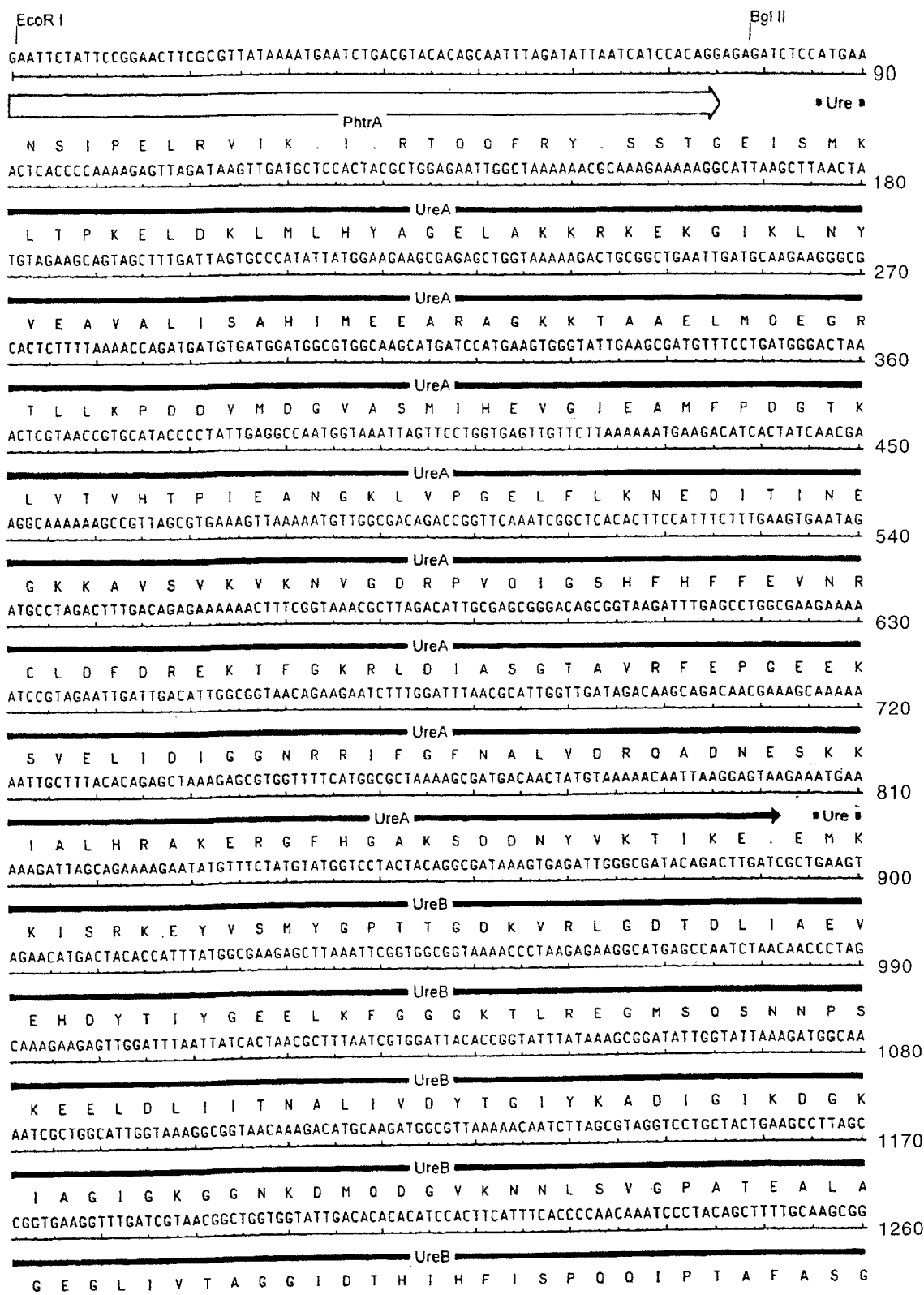
FIG. 4 (1 of 4)

TGTAACAACCATGATTGGTGGTGGAACCGGTCCTGCTGATGGCACTAATGCGACTACTATCACTCCAGGCAGAAGAAATTTAAAATGGAT
                                                                                         ┤ 1350
━━━━━━━━━━━━━━━━━━━━━━━━━━━━━ UreB ━━━━━━━━━━━━━━━━━━━━━━━━━━━━━
  V  T  T  M  I  G  G  G  T  G  P  A  D  G  T  N  A  T  T  I  T  P  G  R  R  N  L  K  W  M
GCTCAGAGCGGCTGAAGAATATTCTATGAATTTAGGTTTCTTGGCTAAAGGTAACGCTTCTAACGATGCGAGCTTAGCCGATCAAATTGA
                                                                                         ┤ 1440
━━━━━━━━━━━━━━━━━━━━━━━━━━━━━ UreB ━━━━━━━━━━━━━━━━━━━━━━━━━━━━━
  L  R  A  A  E  E  Y  S  M  N  L  G  F  L  A  K  G  N  A  S  N  D  A  S  L  A  D  Q  I  E
AGCCGGTGCGATTGGCTTTGCAATTCACGAAGACTGGGGCACCACTCCTTCTGCAATCAATCATGCGTTAGATGTTGCGGACAAATACGA
                                                                                         ┤ 1530
━━━━━━━━━━━━━━━━━━━━━━━━━━━━━ UreB ━━━━━━━━━━━━━━━━━━━━━━━━━━━━━
  A  G  A  I  G  F  A  I  H  E  D  W  G  T  T  P  S  A  I  N  H  A  L  D  V  A  D  K  Y  D
TGTGCAAGTCGCTATCGCCACAGACACTTTGAATGAAGCCGGTTGTGTAGAAGACACTATGGCTGCTATTGCTGGACGCACTATGCACAC
                                                                                         ┤ 1620
━━━━━━━━━━━━━━━━━━━━━━━━━━━━━ UreB ━━━━━━━━━━━━━━━━━━━━━━━━━━━━━
  V  Q  V  A  I  A  T  D  T  L  N  E  A  G  C  V  E  D  T  M  A  A  I  A  G  R  T  M  H  T
TTTCCACACTGAAGGCGCTGGCGGCGGACACGCTCCTGATATTATTAAAGTAGCCGGTGAACACAACATTCTTCCCGCTTCCACTAACCC
                                                                                         ┤ 1710
━━━━━━━━━━━━━━━━━━━━━━━━━━━━━ UreB ━━━━━━━━━━━━━━━━━━━━━━━━━━━━━
  F  H  T  E  G  A  G  G  G  H  A  P  D  I  I  K  V  A  G  E  H  N  I  L  P  A  S  T  N  P
CACCATCCCTTTCACCGTGAATACAGAAGCAGAGCACATGGACATGCTTATGGTGTGCCACCACTTGGATAAAAGCATTAAAGAAGATGT
                                                                                         ┤ 1800
━━━━━━━━━━━━━━━━━━━━━━━━━━━━━ UreB ━━━━━━━━━━━━━━━━━━━━━━━━━━━━━
  T  I  P  F  T  V  N  T  E  A  E  H  M  D  M  L  M  V  C  H  H  L  D  K  S  I  K  E  D  V
           BamHI
            |
TCAGTTCGCTGATTCAAGGATCCGCCCTCAAACCATTGCGGCTGAAGACACTTTGCATGACATGGGGATTTTCTCAATCACCAGTTCTGA
                                                                                         ┤ 1890
━━━━━━━━━━━━━━━━━━━━━━━━━━━━━ UreB ━━━━━━━━━━━━━━━━━━━━━━━━━━━━━
  Q  F  A  D  S  R  I  R  P  Q  T  I  A  A  E  D  T  L  H  D  M  G  I  F  S  I  T  S  S  D
CTCTCAAGCGATGGGCCGTGTGGGTGAAGTTATCACTAGAACTTGGCAAACAGCTGACAAAAACAAGAAAGAATTTGGCCGCTTGAAAGA
                                                                                         ┤ 1980
━━━━━━━━━━━━━━━━━━━━━━━━━━━━━ UreB ━━━━━━━━━━━━━━━━━━━━━━━━━━━━━
  S  Q  A  M  G  R  V  G  E  V  I  T  R  T  W  Q  T  A  D  K  N  K  K  E  F  G  R  L  K  E
AGAAAAAGGCGATAACGACAACTTCAGGATCAAACGCTACTTGTCTAAATACACCATTAACCCAGCGATCGCTCATGGGATTAGCGAGTA
                                                                                         ┤ 2070
━━━━━━━━━━━━━━━━━━━━━━━━━━━━━ UreB ━━━━━━━━━━━━━━━━━━━━━━━━━━━━━
  E  K  G  D  N  D  N  F  R  I  K  R  Y  L  S  K  Y  T  I  N  P  A  I  A  H  G  I  S  E  Y
TGTAGGTTCAGTAGAAGTGGGCAAAGTGGCTGACTTGGTATTGTGGAGTCCAGCATTCTTTGGCGTGAAACCCAACATGATCATCAAAGG
                                                                                         ┤ 2160
━━━━━━━━━━━━━━━━━━━━━━━━━━━━━ UreB ━━━━━━━━━━━━━━━━━━━━━━━━━━━━━
  V  G  S  V  E  V  G  K  V  A  D  L  V  L  W  S  P  A  F  F  G  V  K  P  N  M  I  I  K  G
CGGATTCATTGCGTTAAGCCAAATGGGCGATGCGAACGCTTCTATCCCTACCCCACAACCGGTTTATTACAGAGAAATGTTCGCTCATCA
                                                                                         ┤ 2250
━━━━━━━━━━━━━━━━━━━━━━━━━━━━━ UreB ━━━━━━━━━━━━━━━━━━━━━━━━━━━━━
  G  F  I  A  L  S  Q  M  G  D  A  N  A  S  I  P  T  P  Q  P  V  Y  Y  R  E  M  F  A  H  H
TGGTAAAGCTAAATACGATGCAAACATCACTTTTGTGTCTCAAGCGGCTTATGACAAAGGCATTAAAGAAGAATTAGGACTTGAAAGACA
                                                                                         ┤ 2340
━━━━━━━━━━━━━━━━━━━━━━━━━━━━━ UreB ━━━━━━━━━━━━━━━━━━━━━━━━━━━━━
  G  K  A  K  Y  D  A  N  I  T  F  V  S  Q  A  A  Y  D  K  G  I  K  E  E  L  G  L  E  R  Q
AGTGTTGCCGGTAAAAAATTGCAGAAATATCACTAAAAAAGACATGCAATTCAACGACACTACCGCTCACATTGAAGTCAATCCTGAAAC
                                                                                         ┤ 2430
━━━━━━━━━━━━━━━━━━━━━━━━━━━━━ UreB ━━━━━━━━━━━━━━━━━━━━━━━━━━━━━
  V  L  P  V  K  N  C  R  N  I  T  K  K  D  M  Q  F  N  D  T  T  A  H  I  E  V  N  P  E  T
TTACCATGTGTTCGTGGATGGCAAAGAAGTAACTTCTAAACCAGCCAATAAAGTGAGCTTGGCGCAACTCTTTAGCATTTTCTAGGATTT
                                                                                         ┤ 2520
━━━━━━━━━━━━━━━━━━━━━━━━━━━━━ UreB ━━━━━━━━━━━━━━━━━━━━━━━━━━━━━▶
  Y  H  V  F  V  D  G  K  E  V  T  S  K  P  A  N  K  V  S  L  A  Q  L  F  S  I  F  .  D  F
                BamHI
                 |
TTTAGGAGCAACGCTCCTTAGATCCCCGGGAATTGGGGATCCGCTAGCCCGCCTAATGAGCGGGCTTTTTTTTCTCGGGCAGCGTTGGGT
                                                                                         ┤ 2610
  L  G  A  T  L  L  R  S  P  G  I  G  D  P  L  A  R  L  M  S  G  L  F  F  L  G  Q  R  W  V
```

FIG. 4 (3 of 4)

```
CCTGGCCACGGGTGCGCATGATCGTGCTCCTGTCGTTGAGGACCCGGCTAGGCTGGCGGGGTTGCCTTACTGGTTAGCAGAATGAATCAC
                                                                                          2700
  L  A  T  G  A  H  D  R  A  P  V  V  E  D  P  A  R  L  A  G  L  P  Y  W  L  A  E  .  I  T
CGATACGCGAGCGAACGTGAAGCGACTGCTGCTGCAAAACGTCTGCGACCTGAGCAACAACATGAATGGTCTTCGGTTTCCGTGTTTCGT
                                                                                          2790
  D  T  R  A  N  V  K  R  L  L  L  Q  N  V  C  D  L  S  N  N  M  N  G  L  R  F  P  C  F  V
AAAGTCTGGAAACGCGGAAGTCAGCGCTCTTCCGCTTCCTCGCTCACTGACTCGCTGCGCTCGGTCGTTCGGCTGCGGCGAGCGGTATCA
                                                                                          2880
  K  S  G  N  A  E  V  S  A  L  P  L  P  R  S  L  T  R  C  A  R  S  F  G  C  G  E  R  Y  Q
GCTCACTCAAAGGCGGTAATACGGTTATCCACAGAATCAGGGGATAACGCAGGAAAGAACATGTGAGCAAAAGGCCAGCAAAAGGCCAGG
                                                                                          2970
                                                                         [Origin]
  L  T  Q  R  R  .  Y  G  Y  P  Q  N  Q  G  I  T  Q  E  R  T  C  E  Q  K  A  S  K  R  P  G
AACCGTAAAAAGGCCGCGTTGCTGGCGTTTTTCCATAGGCTCCGCCCCCTGACGAGCATCACAAAAATCGACGCTCAAGTCAGAGGTGG
                                                                                          3060
                              [Origin]
  T  V  K  R  P  R  C  W  R  F  S  I  G  S  A  P  L  T  S  I  T  K  I  D  A  Q  V  R  G  G
CGAAACCCGACAGGACTATAAAGATACCAGGCGTTTCCCCCTGGAAGCTCCCTCGTGCGCTCTCCTGTTCCGACCCTGCCGCTTACCGGA
                                                                                          3150
                              [Origin]
  E  T  R  Q  D  Y  K  D  T  R  R  F  P  L  E  A  P  S  C  A  L  L  F  R  P  C  R  L  P  D
TACCTGTCCGCCTTTCTCCCTTCGGGAAGCGTGGCGCTTTCTCAATGCTCACGCTGTAGGTATCTCAGTTCGGTGTAGGTCGTTCGCTCC
                                                                                          3240
                              [Origin]
  T  C  P  P  F  S  L  R  E  A  W  R  F  L  N  A  H  A  V  G  I  S  V  R  C  R  S  F  A  P
AAGCTGGGCTGTGTGCACGAACCCCCCGTTCAGCCCGACCGCTGCGCCTTATCCGGTAACTATCGTCTTGAGTCCAACCCGGTAAGACAC
                                                                                          3330
                              [Origin]
  S  W  A  V  C  T  N  P  P  F  S  P  T  A  A  P  Y  P  V  T  I  V  L  S  P  T  R  .  D  T
GACTTATCGCCACTGGCAGCAGCCACTGGTAACAGGATTAGCAGAGCGAGGTATGTAGGCGGTGCTACAGAGTTCTTGAAGTGGTGGCCT
                                                                                          3420
                              [Origin]
  T  Y  R  H  W  Q  Q  P  L  V  T  G  L  A  E  R  G  M  .  A  V  L  Q  S  S  .  S  G  G  L
AACTACGGCTACACTAGAAGGACAGTATTTGGTATCTGCGCTCTGCTGAAGCCAGTTACCTTCGGAAAAAGAGTTGGTAGCTCTTGATCC
                                                                                          3510
                              [Origin]
  T  T  A  T  L  E  G  Q  Y  L  V  S  A  L  C  .  S  Q  L  P  S  E  K  E  L  V  A  L  D  P
GGCAAACAAACCACCGCTGGTAGCGGTGGTTTTTTTGTTTGCAAGCAGCAGATTACGCGCAGAAAAAAAGGATCTCAAGAAGATCCTTTG
                                                                                          3600
   [Origin]
  A  N  K  P  P  L  V  A  V  V  F  L  F  A  S  S  R  L  R  A  E  K  K  D  L  K  K  I  L  .
ATCTTTTCTACGGGGTCTGACGCTCAGTGGAACGAAAACTCACGTTAAGGGATTTTGGTCATGAGATTATCAAAAAGGATCTTCACCTAG
                                                                                          3690
  S  F  L  R  G  L  T  L  S  G  T  K  T  H  V  K  G  F  W  S  .  D  Y  Q  K  G  S  S  P  R
ATCCTTTTAAATTAAAAAATGAAGTTTTAAATCAATCTAAAGTATATATGAGTAAACTTGGTCTGACAGTTACCAATGCTTAATCAGTGAG
                                                                                          3780
                                                                    [AmpR]
  S  F  .  I  K  N  E  V  L  N  Q  S  K  V  Y  M  S  K  L  G  L  T  V  T  N  A  .  S  V  R
GCACCTATCTCAGCGATCTGTCTATTTCGTTCATCCATAGTTGCCTGACTCCCCGTCGTGTAGATAACTACGATACGGGAGGGCTTACCA
                                                                                          3870
                              [AmpR]
  H  L  S  Q  R  S  V  Y  F  V  H  P  .  L  P  D  S  P  S  C  R  .  L  R  Y  G  R  A  Y  H
TCTGGCCCCAGTGCTGCAATGATACCGCGAGACCCACGCTCACCGGCTCCAGATTTATCAGCAATAAACCAGCCAGCCGGAAGGGCCGAG
                                                                                          3960
                              [AmpR]
  L  A  P  V  L  Q  .  Y  R  E  T  H  A  H  R  L  Q  I  Y  Q  Q  .  T  S  Q  P  E  G  P  S
CGCAGAAGTGGTCCTGCAACTTTATCCGCCTCCATCCAGTCTATTAATTGTTGCCGGGAAGCTAGAGTAAGTAGTTCGCCAGTTAATAGT
                                                                                          4050
                              [AmpR]
  A  E  V  V  L  Q  L  Y  P  P  P  S  S  L  L  I  V  A  G  K  L  E  .  V  V  R  Q  L  I  V
```

FIG. 4 (4 of 4)

```
                                    Pst I
                                    |
TTGCGCAACGTTGTTGCCATTGCTGCAGGCATCGTGGTGTCACGCTCGTCGTTTGGTATGGCTTCATTCAGCTCCGGTTCCCAACGATCA
                                                                                             4140
━━━━━━━━━━━━━━━━━━━━━━━━━━━━━━━━━━ AmpR ━━━━━━━
   C   A   T   L   L   P   L   L   Q   A   S   W   C   H   A   R   R   L   V   W   L   H   S   A   P   V   P   N   D   Q
AGGCGAGTTACATGATCCCCCATGTTGTGCAAAAAAGCGGTTAGCTCCTTCGGTCCTCCGATCGTTGTCAGAAGTAAGTTGGCCGCAGTG
                                                                                             4230
━━━━━━━━━━━━━━━━━━━━━━━━━━━━━━━━━━ AmpR ━━━━━━━
   G   E   L   H   D   P   P   C   C   A   K   K   R   L   A   P   S   V   L   R   S   L   S   E   V   S   W   P   Q   C
TTATCACTCATGGTTATGGCAGCACTGCATAATTCTCTTACTGTCATGCCATCCGTAAGATGCTTTTCTGTGACTGGTGAGTACTCAACC
                                                                                             4320
━━━━━━━━━━━━━━━━━━━━━━━━━━━━━━━━━━ AmpR ━━━━━━━
   Y   H   S   W   L   W   Q   H   C   I   I   L   L   L   S   C   H   P   .   D   A   F   L   .   L   V   S   T   Q   P
AAGTCATTCTGAGAATAGTGTATGCGGCGACCGAGTTGCTCTTGCCCGGCGTCAACACGGGATAATACCGCGCCACATAGCAGAACTTTA
                                                                                             4410
━━━━━━━━━━━━━━━━━━━━━━━━━━━━━━━━━━ AmpR ━━━━━━━
   S   H   S   E   N   S   V   C   G   D   R   V   A   L   A   R   R   Q   H   G   I   I   P   R   H   I   A   E   L   .
AAAGTGCTCATCATTGGAAAACGTTCTTCGGGGCGAAAACTCTCAAGGATCTTACCGCTGTTGAGATCCAGTTCGATGTAACCCACTCGT
                                                                                             4500
━━━━━━━━━━━━━━━━━━━━━━━━━━━━━━━━━━ AmpR ━━━━━━━
   K   C   S   S   L   E   N   V   L   R   G   E   N   S   Q   G   S   Y   R   C   .   D   P   V   R   C   N   P   L   V
GCACCCAACTGATCTTCAGCATCTTTTACTTTCACCAGCGTTTCTGGGTGAGCAAAAACAGGAAGGCAAAATGCCGCAAAAAAGGGAATA
                                                                                             4590
━━━━━━━━━━━━━━━━━━━━━━━━━━━━━━━━━━ AmpR ━━━━━━━
   H   P   T   D   L   Q   H   L   L   L   S   P   A   F   L   G   E   Q   K   Q   E   G   K   M   P   Q   K   R   E   .
AGGGCGACACGGAAATGTTGAATACTCATACTCTTCCTTTTTCAATATTATTGAAGCATTTATCAGGGTTATTGTCTCATGAGCGGATAC
                                                                                             4680
━━━━━ AmpR ━━━━━━━━━■
   G   R   H   G   N   V   E   Y   S   Y   S   S   F   F   N   I   I   E   A   F   I   R   V   I   V   S   .   A   D   T
ATATTTGAATGTATTTAGAAAAATAAACAAATAGGGGTTCCGCGCACATTTCCCCGAAAAGTGCCACCTGACGTCTAAGAAACCATTATT
                                                                                             4770
   Y   L   N   V   F   R   K   I   N   K   .   G   F   R   A   H   F   P   E   K   C   H   L   T   S   K   K   P   L   L
ATCATGACATTAACCTATAAAAATAGGCGTATCACGAGGCCCTTTCGTCTTCAA
                                                      4824
   S   .   H   .   P   I   K   I   G   V   S   R   G   P   F   V   F   K
```

… # USE OF SALMONELLA VECTORS FOR VACCINATION AGAINST HELICOBACTER INFECTION

This application is a continuation-in-part of PCT/US98/08890, which s filed on Apr. 30, 1998.

BACKGROUND OF THE INVENTION

This invention relates to the use of Salmonella vectors in vaccination methods against Helicobacter infection.

Helicobacter is a genus of spiral, gram-negative bacteria that colonize the gastrointestinal tracts of mammals. Several species colonize the stomach, most notably *H. pylori, H. heilmanii, H. felis,* and *H. mustelae.* Although *H. pylori* is the species most commonly associated with human infection, *H. heilmanii* and *H. felis* have also been isolated from humans, but at lower frequencies than *H. pylori.* Helicobacter infects over 50% of adult populations in developed countries and nearly 100% in developing countries and some Pacific rim countries, making it one of the most prevalent infections worldwide.

Helicobacter is routinely recovered from gastric biopsies of humans with histological evidence of gastritis and peptic ulceration. Indeed, *H. pylori* is now recognized as an important pathogen of humans, in that the chronic gastritis it causes is a risk factor for the development of peptic ulcer diseases and gastric carcinoma. It is thus highly desirable to develop safe and effective methods for preventing and treating Helicobacter infection.

SUMMARY OF THE INVENTION

The invention provides a method of inducing an immune response against Helicobacter in a mammal. This method involves mucosally (e.g., orally) administering to a mammal (e.g., a human) an attenuated Salmonella (e.g., *S. typhi* (e.g., CVD908-htrA or CVD908) or *S. typhimurium* (e.g., BRD509 or BRD807)) vector including a nucleic acid molecule encoding a Helicobacter antigen (e.g., a urease, a urease subunit, or an immunogenic fragment thereof), and parenterally administering to the mammal a Helicobacter antigen (e.g., a urease, a urease subunit, or an immunogenic fragment thereof), optionally, in association with an adjuvant, such as an aluminum compound (e.g., alum). The nucleic acid molecule encoding the Helicobacter antigen can be under the control of a promoter, such as an htrA or a nirB promoter. The antigen used in the mucosal administration can be different from, cross-reactive with, or, preferably, identical to the parenterally administered antigen. In a preferred embodiment, the mucosal administration primes an immune response to an antigen, and the parenteral administration boosts an immune response to the antigen. A mammal treated according to the method of the invention can be at risk of developing, but not have, a Helicobacter infection, or can have a Helicobacter infection. That is, the method can be used to prevent or to treat Helicobacter infection.

The invention also provides an attenuated Salmonella (e.g., *S. typhi* (e.g., CVD908-htrA or CVD908) or *S. typhimurium* (e.g., BRD509 or BRD807)) vector including a nucleic acid molecule encoding a Helicobacter antigen, e.g., a urease, a urease subunit, or an immunogenic fragment thereof, expressed as a fission protein that can be selectively targeted to the outer membrane or secreted from the cell. The nucleic acid molecule encoding the Helicobacter antigen can be under the control of a promoter, such as an htrA or a nirB promoter.

Other features and advantages of the invention will be apparent from the following detailed description, the drawings, and the claims.

BRIEF DESCRIPTION OF THE DRAWINGS

FIG. 4 provides the nucleic acid sequence (SEQ ID NO:1) and amino acid sequence (SEQ ID NO:2) of plasmid pHUR3.

DETAILED DESCRIPTION

Figure 1:
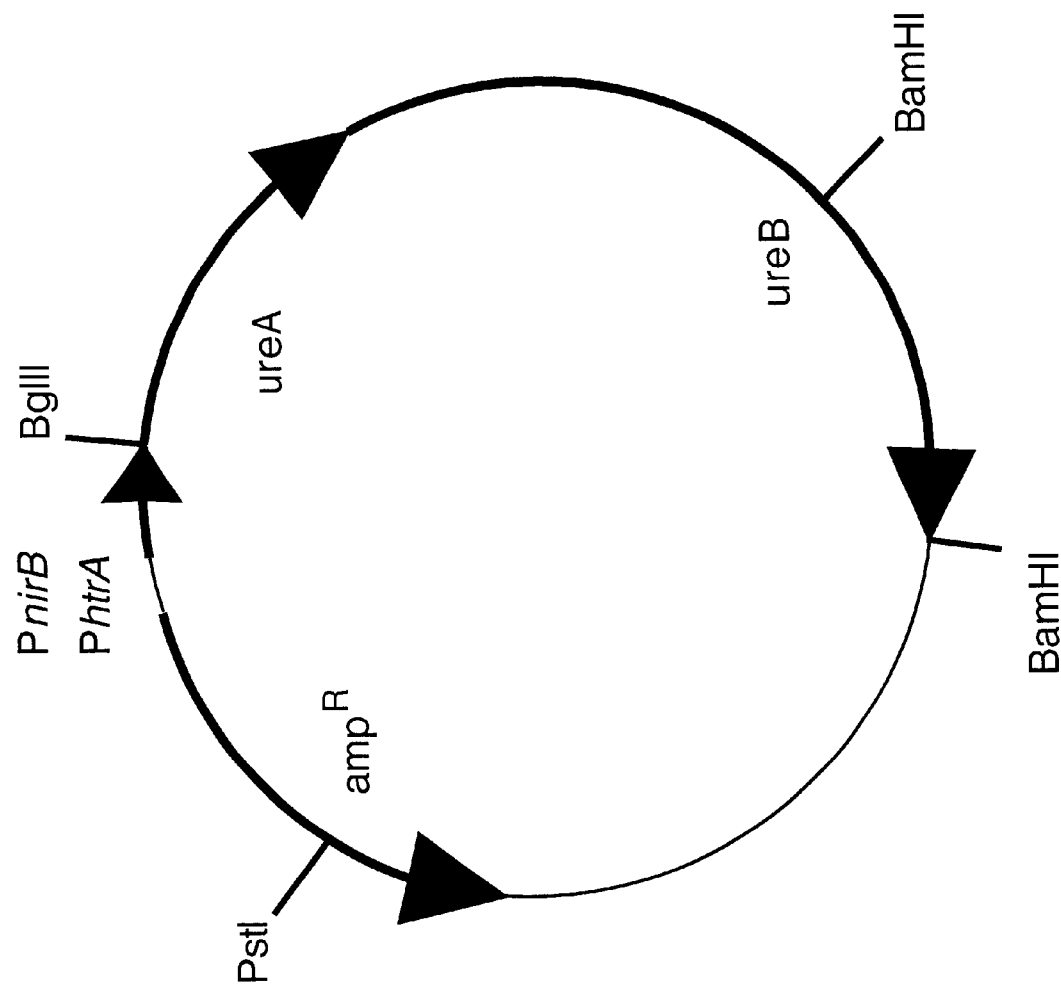
FIG. 1 is a schematic representation of an expression plasmid pH/NUR3) used in Salmonella immunizations.

This invention provides an immunization method against Helicobacter infection that involves: (i) mucosal administration of an attenuated Salmonella vector containing a nucleic acid molecule encoding a Helicobacter antigen, and (ii) parenteral administration of a Helicobacter antigen, preferably, in association with an adjuvant. The method can be used to prevent or to treat Helicobacter infection in a mammal, such as a human. Also, the mucosal administration can be used to prime an immune response to an antigen, and the parenteral administration can be used to boost an immune response to the antigen. The invention also provides Salmonella vectors for use in this method. Salmonella vectors, Helicobacter antigens, and adjuvants that can be used in the method of the invention are first described, as follows. Then, details of the immunization method of the invention, and examples of its efficacy, are provided.

Salmonella Vectors

Numerous attenuated Salmonella vectors that can be used in the invention are known in the art, and can be derived from species such as, for example, *S. typhi, S. typhimurium, S. enteritidis, S. dublin, S. Minnesota,* and *S. choleraesuis.* The vectors can be attenuated chemically (e.g., Ty21a, Swiss Serums and Vaccines, Berna Products) or, preferably, by genetic mutagenesis (e.g., Ty800). For example, attenuation can be achieved by inactivation of key regulatory genes or genes necessary for in vivo survival. For example, the following genes can be inactivated: cya, crp, and asd (cAMP metabolism; see, e.g., Curtiss et al., Vaccine 6:155–160, 1988; Nakayama et al., BioTechnology 6:693, 1988; WO 92/11361), adenylate cyclase and the cAMP receptor (U.S. Pat. No. 5,389,368), cdt (invasion of liver and spleen), phoP/phoQ (two component regulator; see, e.g., Fields et al., Science 243:1059–1062, 1989; U.S. Pat. No. 5,424,065), ompR (control of capsule and porin expression; see, e.g., Dorman et al., Infection and Immunity 57:2136–2140, 1989), outer membrane proteins (U.S. Pat. No. 5,527,529), reverse mutants of streptomycin mutants (U.S. Pat. No. 4,350,684), genes in pathogenicity islands (Shea et al., Infection and Immunity 67:213–219, 1999; WO 99/37759), SPI-2 (invasion of Peyer's patches), Dam (DNA methylation), htrA (heat shock protein; U.S. Pat. No. 5,804,194), and other heat shock proteins (U.S. Pat. No. 5,804,194). The vectors can also be attenuated by auxotrophic mutations, such as mutations in any of the aroA, aroC, aroD (aromatic compounds), purA, or guaAB (purines) genes (see, e.g., U.S. Pat. No. 5,770,214).

Preferably, the mutations in the Salmonella strains used in the invention are non-reverting mutations, i.e., mutations that cannot be repaired in a single step. Mutations of this sort include deletions, inversions, insertions, and substitutions. Preferably, there is more than one mutation in the vector. Methods of making such mutations are well known in the art.

Specific examples of Salmonella vectors that can be used in the invention include *S. typhi* mutant strains, for example, CVD908 *S. typhi* Ty2 ΔaroC/ΔaroD (Hone et al., Vaccine 9:810–816, 1991), CVD908-htrA *S. typhi* Ty2 ΔaroC/ΔaroD/ΔhtrA (Tacket et al., Infection and Immunity 65:452–456, 1997), BRD1116 *S. typhi* Ty2 ΔaroA/ΔaroC/ΔhtrA (Lowe et al., Infection and Immunity 67:700–707, 1999), *S. typhi* ΔaroA/ΔaroE (U.S. Pat. No. 5,770,214; deposited at PHLS, NCTC, 61 Colindale Avenue, London NW9 5HT under Accession No. 25 NCTC 12164), *S. typhi* Ty2 ΔaroA/ΔaroC Km-R (U.S. Pat. No. 5,770,214; deposited at PHLS, NCTC, 61 Colindale Avenue, London NW9 5HT under Accession No. NCTC 12165), and *S. typhi* ΔaroA/ΔaroD (U.S. Pat. No. 5,770,214; deposited at PHLS, NCTC, 61 Colindale Avenue, London NW9 5HT under Accession No. NCTC 122309). It has been shown that one of these, CVD908-htrA, is safe and immunogenic in phase I (Tacket et al., Infection and Immunity 65:452–456, 1997) and phase II studies in a total of 100 adult volunteers.

Specific examples of *S. typhimurium* mutant strains that can be used in the invention include BRD509 *S. typhimurium* ΔaroA/ΔaroD (Strugnell et al., Infection and Immunity 60:3994–4002, 1992), BRD807 *S. typhimurium* ΔaroA/ΔhtrA (Chatfield et al., Microbial Pathogenesis 12:145–151, 1992; U.S. Pat. No. 5,804,194; deposited at PHLS, NCTC, 61 Colindale Avenue, London NW9 5HT under Accession No. NCTC 12459), BRD698 (U.S. Pat. No. 5,804,194; deposited at PHLS, NCTC, 61 Colindale Avenue, London NW9 5HT under Accession No. NCTC 12457), and BRD726 (U.S. Pat. No. 5,804,194; deposited at PHLS, NCTC, 61 Colindale Avenue, London NW9 5HT under Accession No. NCTC 12458).

Additional examples of Salmonella mutant strains that can be used in the invention are described in the following publications: double aro mutants (WO 89/05856, U.S. Pat. No. 5,770,214), htrA mutants (WO 91/15572, U.S. Pat. No. 5,804,194), and ompR mutants (U.S. Pat. No. 5,527,529). Also see, for example, Nakayama et al., BioTechnology 6:693, 1988 and WO 92/11361. In addition, there are numerous alternative strains of *S. typhi* and *S. typhimurium* described in the literature or known in the art that are also attenuated in their virulence, and have been shown to induce immune responses against heterologous antigens. Any of these strains can be used in the method of the present invention.

Any of the attenuated Salmonella strains described above, or others, can be used in the method of the invention to administer a Helicobacter antigen to a mammal for vaccination against Helicobacter infection. This can be accomplished by introducing into the attenuated Salmonella strain a nucleic molecule encoding a Helicobacter antigen. The antigen-encoding nucleic acid molecule to be introduced into the attenuated Salmonella strain can be present, for example, in a plasmid vector (e.g., pHUR3, pHUR4, pNUR3, or pNUR4 (see below)) that includes a regulatory sequence, such as a promoter, and, optionally, a sequence encoding a secretion signal (e.g., a bacterial hemolysin (hly) secretion signal; WO 87/06953, U.S. Pat. No. 5,143,830).

The promoter can be a prokaryotic promoter, for example, a Salmonella promoter, which directs expression of the Helicobacter antigen in the Salmonella vector. Examples of such promoters include the htrA promoter (WO 95/20665), the nirB promoter (WO 92/15689, U.S. Pat. No. 5,547,664), the ssaH promoter (Valdivia et al., Science 277:2007–2011, 1997), the ompR promoter, and any other Salmonella or other bacterial promoter that is upregulated when Salmonella is taken up by mammalian cells. Alternatively, the promoter can be a eukaryotic promoter, such as the cytomegalovirus promoter. Use of such promoters allows for expression of target antigen in a eukaryotic cell, with Salmonella acting as the delivery vehicle for this DNA immunization approach. The construction of such vectors is known in the art. Of course, numerous eukaryotic promoters are known in the art and can be used in the invention.

Introduction of a plasmid into an attenuated Salmonella strain can be accomplished using any of a number of standard methods, such as electroporation or bacteriophage transduction (Turner et al., Infection and Immunity 61:5374–5380, 1993). Also see, e.g., Ausubel et al., *Current Protocols in Molecular Biology*, John Wiley & Sons Inc., 1994, and Ward et al., Infection and Immunity 67(5): 2145–2152, 1999, for methods of introducing plasmids into bacteria, such as Salmonella.

Helicobacter Antigens

Preferred antigens for use in the invention are Helicobacter (e.g., *H. pylori* or *H. felis*) proteins (i.e., peptides or polypeptides), other components Helicobacter (e.g., lipopolysaccharides, carbohydrates, or nucleic acid molecules), or immunogenic fragments thereof. Preferably, the same or a similar (e.g., a fragment) antigen is used in the mucosal administration step as in the parenteral administration step, however, the antigen used in each of these steps can differ. Also, preferably, the mucosally administered antigen primes an immune response to the antigen, and the parenterally administered antigen boosts an immune response to the same antigen. For the mucosal administration step, a nucleic acid molecule (e.g., a DNA molecule) encoding a desired antigen is inserted into an attenuated Salmonella vector, as is described above. For the parenteral administration step, the antigen can be, for example, purified from a bacterial culture or produced using standard recombinant or chemical synthetic methods. Methods for identifying immunogenic fragments of polypeptide antigens are known in the art, and can be employed in preparing antigens for use in the method of the invention (see, e.g., Sturniolo et al., Nature Biotechnology, "Generation of Tissue-Specific and Promiscuous HLA Ligand Databases Using DNA Microarrays and Virtual HLA Class II Matrices," June, 1999). Additional antigens that can be used in the parenteral administration step are whole Helicobacter bacteria and non-purified protein preparations, such as Helicobacter lysates.

The antigens used in the invention can be produced as fusion proteins, which are polypeptides containing amino acid sequences corresponding to two or more proteins (or fragments thereof) that are normally separate proteins, linked together by a peptide bond(s). Fusion proteins generally are synthesized by expression of a hybrid gene, containing nucleotides encoding each of the individual polypeptides that make up the fusion protein. An example of an antigenic fusion protein that can be used in the invention is one that contains a cholera toxin (CT) or an *E. coli* heat-labile toxin (LT) adjuvant (e.g., a toxin A or B subunit, or a fragment or derivative thereof having adjuvant activity) fused to an *H. pylori* antigen, e.g., a urease antigen. Another type of fusion protein included in the invention consists of an antigen fused to a polypeptide (e.g., glutathione S-transferase (GST)) that facilitates purification of the fusion protein. Still another type of fusion protein that can be used in the invention is a fusion with a polypeptide that targets the expressed protein to cells of the immune system. For example, fusions with CD4 or Staph A can be used. Proteins used as antigens in the invention can also be covalently coupled or chemically cross-linked to adjuvants, using standard methods.

The most preferred *H. pylori* antigens for use in the invention are urease antigens, which include, e.g., immunogenic fragments or subunits (e.g., UreA or UreB) of urease. Most preferred urease antigens are enzymatically inactive, recombinant multimeric urease complexes, produced as described in Lee et al., WO 96/33732. A number of other immunogenic H. pylori antigens can be administered according to the invention, e.g., catalase (WO 95/27506), HspA and HspB (WO 94/26901), lactoferrin receptor (WO 97/13784), p76 (WO 97/12908), p32 (WO 97/12909), BabA and BabB (WO 97/47646), AlpA (WO 96/41880), AlpB (WO 97/11182), as well as the antigens described in WO 96/38475, WO 96/40893, WO 97/19098, WO 97/37044, WO 98/18323, WO 97/37044, WO 97/4764, WO 98/04702, and WO 98/32768. Additional preferred antigens for use in the invention are GHPO 1516, GHPO 789, GHPO 386, GHPO 1615, GHPO 1360, GHPO 1320, GHPO 639, GHPO 792, GHPO 536, GHPO 525, GHPO 1275, GHPO 1688, GHPO 706, GHPO 419, GHPO 1595, GHPO 1398, GHPO 986, GHPO 1282, GHPO 1056, GHPO 1443, GHPO 13, GHPO 109, GHPO 257, GHPO 1034, GHPO 236, GHPO 1166, GHPO 1351, and GHPO 1420 (WO 98/21225, WO 98/43478, and WO 98/43479), as well as other antigens described in these publications.

Adjuvants

Although not required, the attenuated Salmonella vectors described above for mucosal administration step can be administered with a mucosal adjuvant. The adjuvant can be admixed with the Salmonella vector or expressed in the Salmonella vector (e.g., as a fusion protein with an antigen, see above), either from an integrated nucleic acid molecule or episomally, e.g., on a plasmid. Such adjuvants can be chosen from bacterial toxins, e.g., the cholera toxin (CT), the *E. coli* heat-labile toxin (LT), the *Clostridium difficile* toxin, and the Pertussis toxin (PT), or combinations, subunits, toxoids, fragments, homologs, derivatives, fusions, or mutants that are derived therefrom and have adjuvant activity. For example, it is possible to use a purified preparation of the native cholera toxin B subunit (CTB) or a polypeptide including the carboxyl-terminal repeats of *C. difficile* toxin A (WO 97/02836). Preferably, a mutant is used in which toxicity is reduced. Such mutants are described in, e.g., WO 95/17211 (mutant CT Arg-7-Lys), WO 96/6627 (mutant LT Arg-192-Gly), and WO 95/34323 (mutant PT Arg-9-Lys and Glu-129-Gly). Other LT mutants that can be used include at least one of the following mutations: Ser-63-Lys, Ala-69-Gly, Glu-110-Asp, and Glu-112-Asp. Other compounds, such as MPLA, PLGA, and QS-21, can also be used as adjuvants for the mucosal route.

Adjuvants for use in parenteral administration include, for example, aluminum compounds (e.g., alum), such as aluminum hydroxide, aluminum phosphate, and aluminum hydroxy phosphate. The antigen can be precipitated with, or adsorbed onto, the aluminum compound using standard methods.

In addition to aluminum compounds, a large number of appropriate adjuvants for administration by the systemic or parenteral route exist in the art and can be used in the invention. For example, liposomes; ISCOMS; microspheres; protein chochleates; vesicles consisting of nonionic surfactants; cationic amphiphilic dispersions in water; oil/water emulsions; muramidyldipeptide (MDP) and its derivatives, such as glucosyl muramidyldipeptide (GMDP), threonyl-MDP, murametide, and murapalmitin; QuilA and its subfractions; as well as various other compounds, such as DC-chol; monophosphoryl-lipid A (MPLA) major lipopolysaccharide from the wall of a bacterium, for example, *E. coli, S. minnesota, S. typhimurium, Shigella flexneri,* or *N. meningitidus;* algan-glucan; gamma-inulin; calcitriol; and loxoribine can be used. Other adjuvants, such as RIBI (ImmunoChem, Hamilton, MT) and polyphosphazene (WO 95/2415), can also be used in parenteral administration.

Useful liposomes for the purposes of the present invention can be selected, for example, from pH-sensitive liposomes, such as those formed by mixing cholesterol hemisuccinate (CHEMS) and dioleyl phosphatidyl ethanolamine (DOPE); liposomes containing cationic lipids recognized for their fusiogenic properties, such as 3-beta-(N-(N',N'-dimethylamino-ethane)carbamoyl)cholesterol (DC-chol) and its equivalents, which are described in U.S. Pat. No. 5,283,185 and WO 96/14831; dimethyldioctadecylammonium bromide (DDAB) and the BAY compounds described in EP 91645 and EP 206 037, for example, Bay R1005 (N-(2-deoxy-2-L-leucylamino-beta-D-glucopyranosyl)-N-octa-decyldodecanoylamide acetate; and liposomes containing MTP-PE, a lipophilic derivative of MDP (muramidyldipeptide). These liposomes are useful as adjuvants with all of the antigens described herein.

Useful ISCOMs for the purposes of the present invention can be selected, for example, from those compounds of QuilA or of QS-21 combined with cholesterol and, optionally, also with a phospholipid, such as phosphatidylcholine. These are particularly advantageous for the formulation of the lipid-containing antigens.

Useful microspheres for the purposes of the present invention can be formed, for example, from compounds such as polylactide-co-glycolide (PLAGA), alginate, chitosan, polyphosphazene, and numerous other polymers.

Useful protein chochleates for the purposes of the present invention can be selected, for example, from those formed from cholesterol and, optionally, an additional phospholipid, such as phosphatidylcholine. These are especially advantageous for the formulation of the lipid-containing antigens.

Useful vesicles consisting of nonionic surfactants for the purposes of the present invention can be, for example, formed by a mixture of 1-mono-palmitoyl glycerol, cholesterol, and dicetylphosphate. They are an alternative to conventional liposomes, and can be used for the formulation of all of the antigens described herein.

Useful oil/water emulsions for the purposes of the present invention can be selected, for example, from MF59 (Biocine-Chiron), SAF1 (Syntex), and the montanides ISA51 and ISA720 (Seppic).

A useful adjuvant for the purposes of the present invention can also be a fraction derived from the bark of the South American tree Quillaja Saponaria Molina, for example, QS-21, a fraction purified by HPLC chromatography as is described in U.S. Pat. No. 5,057,540. Since some toxicity may be associated with QS-21, it may be advantageous to use it in liposomes based on sterol, as is described in WO 96/33739.

Induction of an Immune Response Against Helicobacter

The method of the invention can be used to prevent Helicobacter infection in a patient, as well as to treat an ongoing Helicobacter infection in a patient. Thus, gastroduodenal diseases associated with these infections, including acute, chronic, or atrophic gastritis, and peptic ulcers, e.g., gastric or duodenal ulcers, can be prevented or treated using the method of the invention.

As is noted above, the method of the invention involves mucosal (e.g., oral, intranasal, intragastric, pulmonary, intestinal, rectal, ocular, vaginal, or urinary tract) administration of a Salmonella vector including a nucleic acid molecule that encodes a Helicobacter antigen, followed by parenteral (e.g., intramuscular, subcutaneous, intradermal, intraepidermal, intravenous, or intraperitoneal) administration of a Helicobacter antigen, preferably in association with an adjuvant. The antigen used in the mucosal prime can be different from, cross-reactive with, or, preferably, identical to the parenterally administered antigen. Preferably, the mucosal administration step primes an immune response to an antigen, and the parenteral administration step boosts an immune response to the antigen. Also included in the invention are vaccination methods involving parenteral priming and mucosal boosting (e.g., with a Salmonella vector including a nucleic acid molecule encoding a Helicobacter antigen), and parenteral administration of a Salmonella vector including a nucleic acid molecule encoding a Helicobacter antigen.

Attenuated Salmonella vectors, antigens, formulations, adjuvants, administration regimens, specific mucosal and parenteral routes, and dosages to be used in the method of the invention can readily be determined by one skilled in the art. For example, $5 \times 10^6$–$5 \times 10^{10}$ colony forming units, e.g., $5 \times 10^8$ colony forming units, of an attenuated Salmonella vector can be used in the mucosal administration, and 5–1000 μg, e.g., 100 μg, antigen, can be used in the parenteral administration. The mucosal administration can take place only once or two or more (e.g., three, four, or five) times, for example, separated by two, three, or four days or weeks. Similarly, the parenteral administration can take place once or two or more (e.g., three, four, or five) times, separated by weeks, months, or years from each other or the mucosal administration.

In one example of an immunization regimen that can be used, a patient is primed with two doses of an attenuated Salmonella vector (e.g., S. typhi CVD908-htrA or CVD908, or S. typhimurium BRD509 or BRD807) expressing an antigen (e.g., urease from plasmid pHUR3, pHUR4, pNUR3, or pNUR4) on days 0 and 21, and then parenterally boosted on day 51 or later with an antigen (e.g., urease) and an adjuvant (e.g., alum). The details of construction of pHUR3 and pNUR3, which each include an ampicillin resistance gene, are described below. pHUR4 and pNUR4 are constructed by removing the ampicillin resistance gene from pHUR3 and pNUR3, respectively, by digestion with the restriction endonuclease RcaI, and cloning into the digested vectors a kanamycin resistance gene that can be obtained from plasmid pUC4K (Pharmacia) by digestion with EcoRI.

A useful pharmaceutical composition for the purposes of the present invention can be manufactured in a conventional manner. In particular, it can be formulated with a pharmaceutically acceptable carrier or diluent, e.g., water or a saline solution. In general, the diluent or carrier can be selected according to the mode and route of administration and according to standard pharmaceutical practices. Appropriate carriers or diluents, as well as what is essential for the preparation of a pharmaceutical composition, are described, e.g., in Remington's Pharmaceutical Sciences ($18^{th}$ edition), ed. A. Gennaro, 1990, Mack Publishing Company, Easton, Pa., a standard reference book in this field. As a specific example, the attenuated Salmonella vectors of the invention can be formulated in a tablet for oral administration (see, e.g., U.S. Pat. No. 5,804,194).

The therapeutic or prophylactic efficacy of the method of the invention can be evaluated according to standard methods, e.g., by measuring the induction of an immune response or the induction of therapeutic or protective immunity using, e.g., the mouse/H. felis model and the procedures described in Lee et al., Eur. J. Gastroenterology and Hepatology 7:303, 1995 or Lee et al., J. Infect. Dis. 172:161, 1995. Persons skilled in this art will realize that H. felis can be replaced in the mouse model by another Helicobacter species. For example, the efficacy of the method is, preferably, evaluated in a mouse model using an H. pylori strain adapted to mice. The efficacy can be determined by comparing the level of infection in gastric tissue (e.g., by measuring the urease activity, bacterial load, or condition of the gastritis) with that in a control group. A therapeutic effect or a protective effect exists when infection is reduced compared with a control group. Experimental methods and results showing the efficacy of the present method is described as follows.

Experimental Methods and Results

Construction of ureAB expression plasmids under the control of the nirB and htrA promoters—Method 1

A ureAB expression plasmid is constructed by subcloning a PCR product containing the ureAB genes (amplified from plasmid pORV273) into plasmid vector ptetnir15. Plasmid pORV273 is obtained from OraVax, Inc., Cambridge, Mass. Plasmid ptetnir15 has been described (Chatfield et al., Bio/Technology 10:888–892, 1992; Oxer et al., Nucl. Acids Res. 19:1889–1892, 1991). This vector was modified by standard techniques known in the art, to introduce into the vector a suitable restriction site for subcloning other genes for optimal expression under control of the nirB promoter. An NcoI site was introduced 10 basepairs 3' to the Shine-Dalgarno sequence of ptetnir15, and the resultant plasmid is designated ptetnir15/mod. Plasmid ptetnir15/mod, carried in strain BRD940, is obtained from Peptide Therapeutics Ltd., Cambridge, U.K.

The ureAB gene is amplified by PCR from pORV273 using Turbo Pfu polymerase (Stratagene), which has 3'-5' proof-reading activity, and two primers, designated orafor and orarev. Primer orafor introduces EcoRI and BspHI sites immediately upstream of the initiating codon of the ureA gene. Primer orarev binds approximately 18 basepairs downstream of the BamHI site that is located 45 basepairs downstream of the termination codon of the ureB gene.

The PCR reaction includes 0.1 μg pORV273 and 100 pmol each of primers orafor (5'-TAG GGA ATT CTC ATG AAA CTC ACC CCA AAA G-3' (SEQ ID NO:3)) and orarev (5'-GCC AAC TTA GCT TCC TTT CGG G-3' (SEQ ID NO:4)) per 100 μl reaction and utilizes 25 cycles, with an annealing temperature of 50° C. The resulting 2.4 kb PCR product is purified from a 1% agarose gel using a Qiaquick gel extraction kit (Qiagen). As is described below, the actual method used in the generation of pNUR and pHUR differed from this description in the sequence of orarev. Therefore, the method described here may need to be adapted in ways known to those skilled in the art by changing, for example, the precise annealing temperature or the number of cycles required to give sufficient product, or even in the sequence of the primer orarev.

The PCR product is digested with BspHI+BamHI, and purified with a Promega Wizard DNA clean-up kit. Plasmid ptetnir15/mod is digested with NcoI+BamHI (the NcoI site is 10 basepairs 3' to the Shine-Dalgarno sequence of ptetnir15, and generates a cohesive end that is compatible with BspHI), and dephosphorylated using shrimp alkaline phosphatase. The largest fragment from the digestion of ptetnir 15/mod is isolated from a 1% agarose gel using a Qiaquick gel extraction kit (Qiagen), and ligated to the digested PCR product using the Ligator Express Kit (Clontech). Ligations are transformed into electrocompetent E. coli TG1cells (Stratagene).

Plasmids from ampicillin-resistant transformants are screened for the presence of the full length, 2.4 kb ureAB gene by restriction analysis. The ureAB gene from plasmid pORV273 has a BamHI site within the coding sequence. However, in a small number of ptetnir 15/mod+ureAB transformants, incomplete digestion or re-ligation of the two ureAB fragments yields the full length ureAB PCR product. The orientation of the ureAB gene in the ptetnir15-derived plasmid is confirmed by PCR, and a plasmid with the full length ureAB gene, in the correct orientation is designated pNUR.

The nirB promoter in plasmid pNUR is replaced with the htrA promoter from phtrAcore, which is obtained from Peptide Therapeutics Ltd., Cambridge, U.K. Plasmids pNUR and phtrAcore are digested with PstI and Bg/II. Digested pNUR is dephosphorylated with shrimp alkaline phosphatase. The digestion products are run on a 1% agarose gel, and a 0.8 kb fragment containing the htrA promoter from the phtrAcore digestion and the 4.0 kb fragment from pNUR lacking the nirB promoter are extracted from the gel using a Qiagen Qiaquick gel extraction kit. The two fragments are ligated together (Clontech Ligator express kit), and transformed into electrocompetent E. coli TG1 cells (Stratagene). Transformants are screened for the presence of the htrA promoter by PCR using primer pairs specific for htrA (5902/5904) or nirB (5901/5904). A plasmid with the htrA promoter and a full length ureAB gene is designated pHUR.

The nucleotide sequence across the promoter region and ureAB genes of final plasmids are confirmed. Samples of the plasmids are prepared using the Qiagen "Plasmid midi kit" (Catalog No. 12143), and the DNA sequence determined by standard techniques. Oligonucleotides 5901 to 5919 (see below) can be used, and allow nucleotide sequence determination of both DNA strands. Oligonucleotides 5901 and 5902 hybridize within nirB and htrA, respectively, while 5919 hybridizes within ptetnir15/mod, downstream of the ureAB genes. The other oligonucleotides hybridize within the ureAB genes. The data confirm that the nucleotide sequence across the recombinant region of all plasmids are as expected.

Plasmids pNUR and pHUR are introduced into S. typhimurium strains such as, e.g., BRD509 and BRD807, and S. typhi strains such as, e.g., CVD908 and BRD948, by electroporation and selection of ampicillin-resistant colonies.

Construction of ureAB Expression Plasmids Under the Control of the nirB and htrA Promoters—Method 2

The protocol described above is one example of many by which one skilled in the art can derive an expression plasmid suitable for directing the synthesis of an H. pylori antigen, e.g., urease, under the control of the htrA or nirB promoter in an attenuated strain of Salmonella. Alternative primers can be used in the PCR amplification of the genes from the starting plasmid, and alternative strategies for the introduction of the gene via alternative restriction sites are possible. One such alternative was employed in the construction of plasmids pNUR3 and pHUR3. During the design of the primers for PCR, a sequence error in the database-deposited gene sequence caused the 3' end of the ureB gene to be incorrectly identified. A primer was synthesized for the PCR amplification that, in fact, resulted in a non-native sequence of the gene, containing an additional 49 codons after the genuine termination codon. This error was subsequently corrected by the method described below, yielding a final plasmid with a sequence identical to that of the plasmid that would be produced by the strategy described above. This method is described in further detail, as follows.

As is described above, plasmid pORV273 was obtained from OraVax Inc. Plasmid ptetnir 15 has been described (Chatfield et al., Bio/Technology 10:888–892, 1992; Oxer et al., Nucl. Acids Res. 19:1889–1892, 1991), and this vector was modified by standard techniques, to introduce into the vector a suitable restriction site for subcloning other genes for optimal expression under control of the nirB promoter. An NcoI site was introduced 10 basepairs 3' to the Shine-Dalgarno sequence of ptetnir15, and the resultant plasmid was designated ptetnir 15/mod. Plasmid ptetnir15/mod, carried in strain BRD940, was obtained from the culture collection of Peptide Therapeutics Ltd., Cambridge, U.K.

The ureAB gene was amplified by PCR from pORV273 using Turbo Pfu polymerase (Stratagene), which has 3'-5' proof-reading activity and two primers, designated orafor and orarev. Primer orafor introduces EcoRi and BspHI sites immediately upstream of the initiating codon of the ureA gene. Primer orarev introduces a BamHI and a PstI site just before the correct 3' end of the ureAB gene. Subsequent digestion and cloning, as is described below, resulted in the deletion of the correct termination codon of ureB, with the result that transcription continued into the vector sequence until an in-frame stop codon was reached, adding 49 amino acids to the translated protein.

The PCR reaction included 0.1 μg pORV273 and 100 pmol each of primers orafor (5'-TAG GGA ATT CTC ATG AAA CTC ACC CCA AAA G-3' (SEQ ID NO:3)) and orarev (5'-TCT ACT GCA GGA TCC AAA ATG CTA AAG AGT TGC G-3' (SEQ ID NO:5)) per 100 μl reaction, and utilized 25 cycles, with an annealing temperature of 50° C. The resulting 2.4 kb PCR product was purified from a 1% agarose gel using a Qiaquick gel extraction kit (Qiagen). The PCR product was digested with BspHI+BamHI, and purified with a Promega Wizard DNA clean-up kit. Plasmid ptetnir15/mod was digested with NcoI+BamHI (the NcoI site is 10 basepairs 3' to the Shine-Dalgarno sequence of ptetnir15, and generates a cohesive end that is compatible with BspHI), and dephosphorylated using shrimp alkaline phosphatase. The largest fragment from the digestion of ptetnir 15/mod was isolated from a 1% agarose gel using a Qiaquick gel extraction kit (Qiagen), and ligated to the digested PCR product using the Ligator Express Kit (Clontech). Ligations were transformed into electrocompetent E. coli TG1 cells (Stratagene).

Plasmids from ampicillin-resistant transformants were screened for the presence of the full length, 2.4 kb ureAB gene by restriction analysis. The ureAB gene from plasmid pORV273 has a BamHI site within the coding sequence. However, in a small number of ptetnir15/mod+ureAB transformants, incomplete digestion or re-ligation of the two ureAB fragments yielded the full length ureAB PCR product. The orientation of the ureAB gene in the ptetnir15-derived plasmid was confirmed by PCR and a plasmid with the full length ureAB gene, in the correct orientation was designated pNUR1.

The nirB promoter in plasmid pNUR1 was replaced with the htrA promoter from phtrAcore, which is obtained from Peptide Therapeutics Ltd., Cambridge, U.K. Plasmids pNUR1 and phtrAcore were digested with PstI and BglII. Digested pNUR1 was dephosphorylated with shrimp alkaline phosphatase. The digests were run on a 1% agarose gel, and a 0.8 kb fragment containing the htrA promoter from the phtrAcore digest and the 4.0 kb fragment from pNUR1 lacking the nirB promoter were extracted from the gel using a Qiagen Qiaquick gel extraction kit. The two fragments were ligated together (Clontech Ligator express kit) and transformed into electrocompetent E. coli TG1 cells (Stratagene). Transformants were screened for the presence of the htrA promoter by PCR using primer pairs specific for htrA (5902/5904) or nirB (5901/5904). A plasmid with the htrA promoter and a full length ureAB gene was designated pHUR1.

Subsequent to this it was discovered that there had been a cloning error in the 3' terminal portion of ureB, resulting in a translated product with an additional 49 amino acids from both pHUR1 and pNUR1. This was corrected by replacing the small BamHI fragment containing the C-terminus of the ureB gene with the corresponding, and correct, fragment from pORV272. pORV273, pHUR1, and pNUR1 were digested with BamHI, and the small fragment from the pORV273 digestion was ligated to the large fragment from the pHUR1 and pNUR1 digestions. Clones were screened for orientation of the insert, and clones with the correct orientation were designated pHUR3 and pNUR3. These clones were characterized by full nucleotide sequencing of the region including the promoter and the complete ureAB gene on both strands, and found to be correct.

The nucleotide sequences across the nirB promoter and ureAB genes of pNUR1 and of the htrA promoter region of pHUR1 were confirmed. Samples of the two plasmids were prepared using the Qiagen "Plasmid midi kit" (Catalogue No. 12143), and the DNA sequence was determined by standard techniques known in the art. Oligonucleotides 5901 to 5919 were used, which allow nucleotide sequence determination of both DNA strands. Oligonucleotides 5901 and 5902 hybridize within nirB and htrA, respectively, while 5919 hybridizes within ptetnir 15/mod downstream of the ureAB genes. The other oligonucleotides hybridize within the ureAB genes. These were diluted to 1 pmol $\mu l^{-1}$, packed in dry ice with the plasmid samples, and sent to Cambridge Bioscience (Cambridge) for nucleotide sequence determination. The data confirmed that the nucleotide sequence across the recombinant region of all three plasmids was as expected.

Sequences of primers that can be used in the invention, as is described above, are as follows.
5901
Primes within nirB promoter ~60 basepairs upstream of SD sequence
TCA AAT GGT ACC CCT TGC TGA (SEQ ID NO:6)
5902
Primes within htrA promoter ~60 basepairs upstream of SD sequence
TAT TCC GGA ACT TCG CGT TA (SEQ ID NO:7)
5903
Primes ~250 basepairs downstream from start of urea gene
TGT TTC CTG ATG GGA CTA AAC TC (SEQ ID NO:8)
5904
Reverse primes ~300 basepairs downstream from start of urea gene
ACC AGG AAC TAA TTT ACC ATT G (SEQ ID NO:9)
5905
Primes ~550 basepairs downstream from start of urea gene
TTG ATT GAC ATT GGC GGT AAC (SEQ ID NO:10)
5906
Reverse primes ~600 basepairs from start of urea gene
GTT GTC TGC TTG TCT ATC AAC C (SEQ ID NO:11)
5907
Primes ~150 basepairs downstream from start of ureB gene
GGT GGC GGT AAA ACC CTA AGA G (SEQ ID NO:12)
5908
Reverse primes ~180 basepairs downstream of ureB gene
CTT TGC TAG GGT TGT TAG ATT G (SEQ ID NO:13)
5909
Primes ~400 basepairs downstream from start of ureB gene
AAT CCC TAC AGC TTT TGC AAG C (SEQ ID NO:14)
5910
Reverse primes ~500 basepairs from start of ureB gene
GTG CCA TCA GCA GGA CCG GTT C (SEQ ID NO:15)
5911
Primes ~750 basepairs from start of ureB gene
ATC GCC ACA GAC ACT TTG AAT G (SEQ ID NO:16)
5912
Reverse primes ~820 basepairs downstream from start of ureB gene
TAG CAG CCA TAG TGT CTT CTA C (SEQ ID NO:17)
5913
Primes ~1050 basepairs downstream from start of ureB gene
TGA AGA CAC TTT GCA TGA CAT G (SEQ ID NO:18)
5914
Reverse primes 1080 basepairs downstream of ureB gene
TGA GAG TCA GAA CTG GTG ATT G (SEQ ID NO:19)
5915
Primes ~1350 basepairs downstream from start of ureB gene
CAT GAT CAT CAA AGG CGG ATT C (SEQ ID NO:20)
5916
Reverse primes ~1380 basepairs downstream from start of ureB
GAA GCG TTC GCA TCG CCC ATT TG (SEQ ID NO:21)
5917
Primes ~1650 basepairs from start of ureB
TCG TGG ATG GCA AAG AAG TAA C (SEQ ID NO:22)
5918
Reverse primes ~1680 basepairs from start of ureB
GCG CCA AGC TCA CTT TAT TG (SEQ ID NO:23)
5919
Reverse primes 80 basepairs downstream of BamHI site downstream of ureB
CAA CGA CAG GAG CAC GAT CAT G (SEQ ID NO:24)

Figure 5:
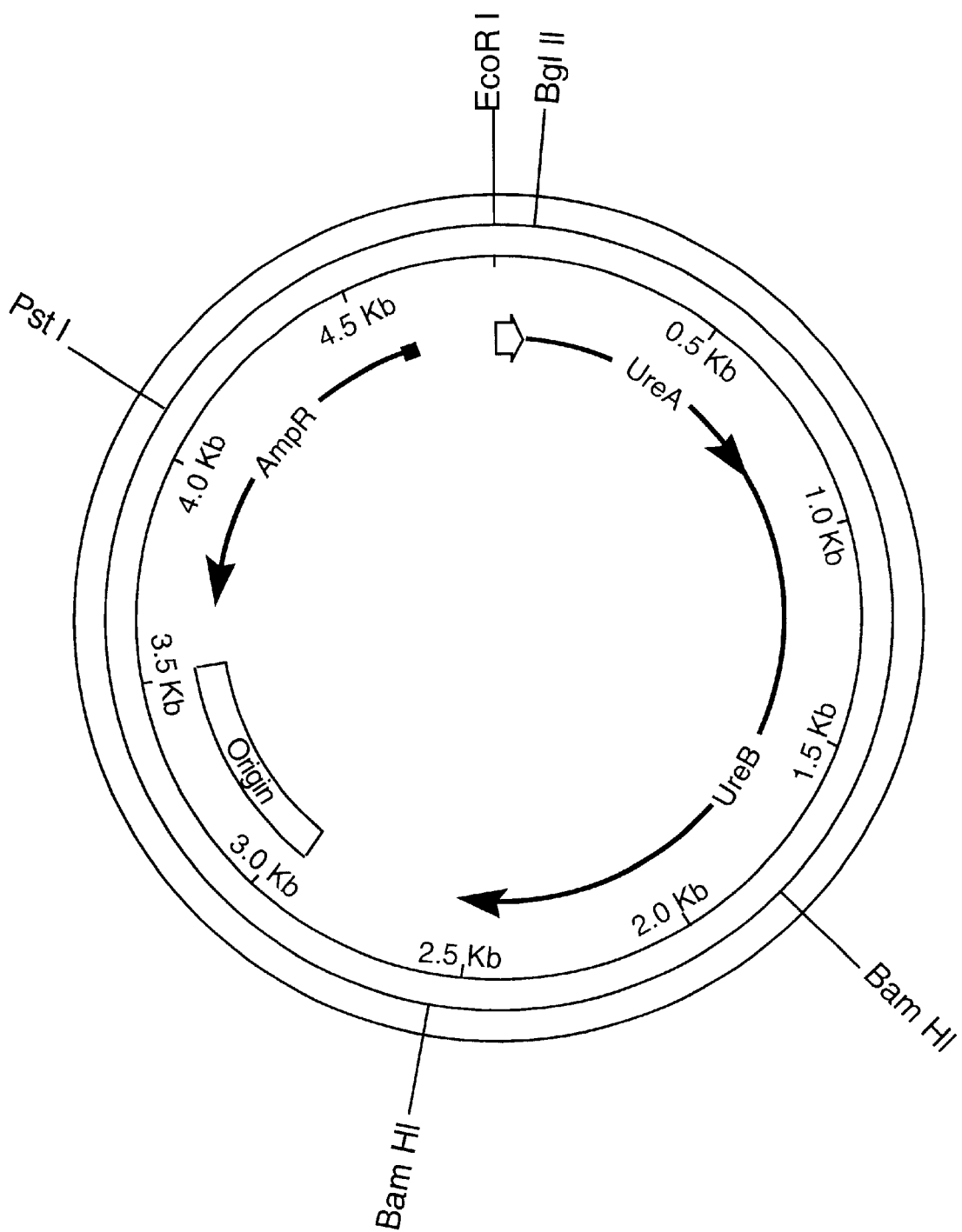
FIG. 5 is a schematic representation of some relevant features of pHUR3.

The nucleotide sequences across the promoter regions and ureAB genes of the final plasmids, pHUR3 and pNUR3, were also confirmed. E. coli MC1061 cells containing the plasmids were sent to Cambridge Biosciences Ltd., who prepared plasmid DNA and determined the nucleotide sequences of the promoter and ureAB genes of both plasmids. The data confirmed that the nucleotide sequence across the relevant region of both plasmids was as expected. The sequence of plasmid pHUR3 is shown in FIG. 4, and a plasmid map showing its relevant features is provided in FIG. 5.

Plasmids pNUR and pHUR were introduced into *S. typhimurium* strains BRD509 and BRD807, and *S. typhi* strains CVD908 and BRD948, by electroporation and selection of ampicillin-resistant colonies.

Immunization and Protection Experiments

Figure 2A:
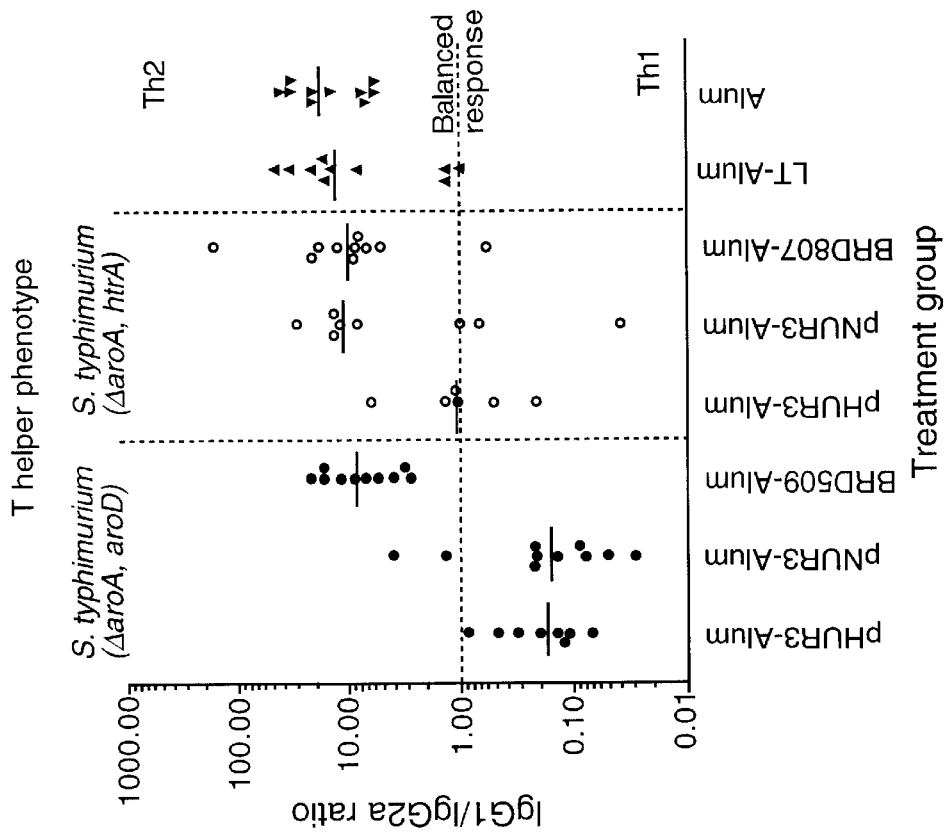
FIG. 2A is a graph showing the urease-specific serum antibody (IgG2a) response of mice that were mucosally primed with *S. typhimurium*-vectored urease, followed by parenteral boosting with urease and alum.
Figure 2B:
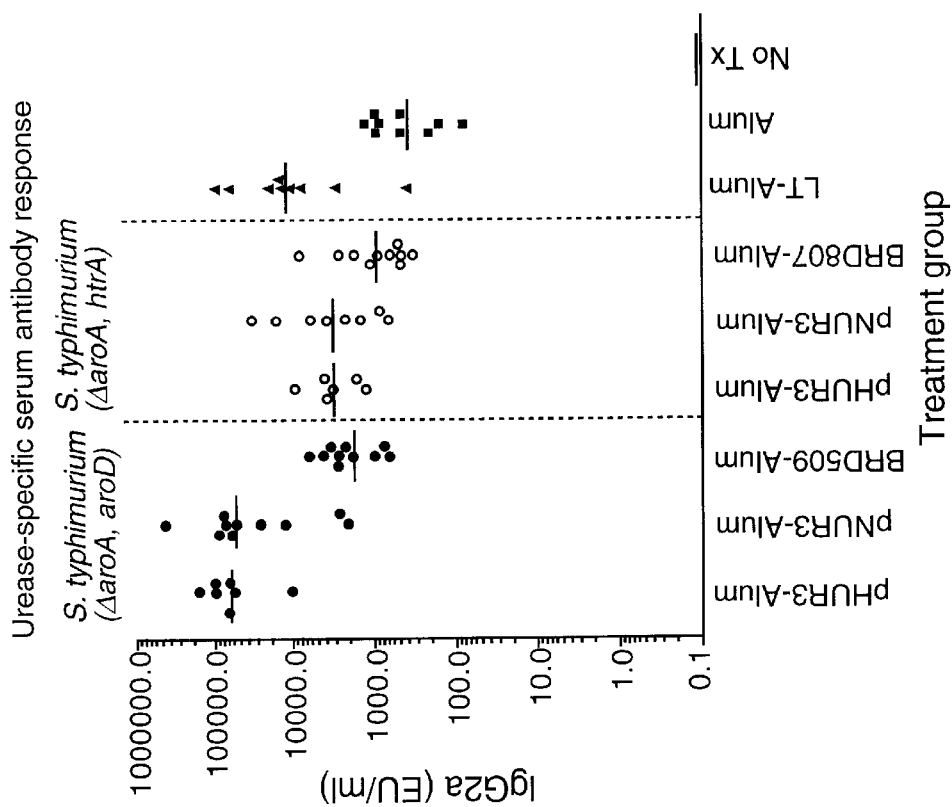
FIG. 2B is a graph showing the T helper phenotype (IgG1/IgG2a ratio) of mice that were mucosally primed with *S. typhimurium*-vectored urease, followed by parenteral boosting with urease and alum.

Inbred Balb/C mice were immunized by the intragastric route with live, attenuated *Salmonella typhimurium* (1E10 CFU/ml) expressing urease apoenzyme on day 0 (FIG. 1). Animals were boosted twice on days 21 and 35 with 10 μg soluble, recombinant urease plus aluminum hydroxide (200 μg) by the parenteral route. Fourteen days later, serum antibody responses to urease were measured. Controls included: (1) prime-boost with the Salmonella parental control strains (BRD509 ΔaroA/ΔaroD (Strugnell et al., Infection and Immunity 60:3994–4002, 1992) and BRD807ΔaroA/ΔhtrA (Chatfield et al., Microbial Pathogenesis 12:145–151, 1992)) minus the urease construct, (2) mucosal priming with LT in place of Salmonella (gold standard), and (3) parenteral immunization with urease plus alum alone. Attenuated *S. typhimurium* (ΔaroA/ΔaroD) expressing urease under the transcriptional control of either an htrA promoter (pHUR3) or the nirB promoter (pNUR3) induced an elevated IgG2a response against urease that was greater than the gold standard using LT-Alum (FIG. 2A). A comparable response to LT-Alum was induced with *S. typhimurium* (ΔaroA/ΔhtrA) carrying the same urease constructs (FIG. 2A). Analysis of the IgG1/IgG2a ratio demonstrated the induction of a Th1 response with the double aro mutant, and a more balanced response with the Δaro/ΔhtrA mutant strain (FIG. 2B). Urease-specific antibody in FIG. 2A is expressed as EU/ml on a logarithmic scale and median response is indicated by the bar.

Figure 3B:
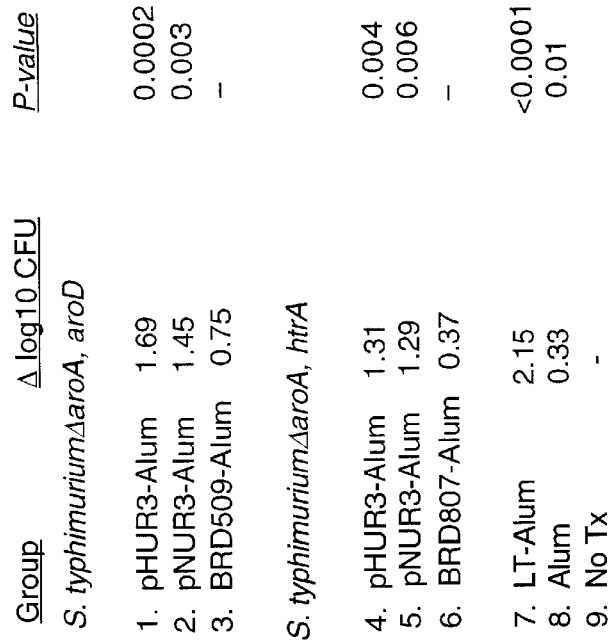
FIG. 3B is a table showing protection against Helicobacter infection in mice that were mucosally primed with *S. typhimurium*-vectored urease, followed by parenteral boosting with urease and alum, as $\log_{10}$ reduction in comparison to a no treatment control group.
Figure 3A:
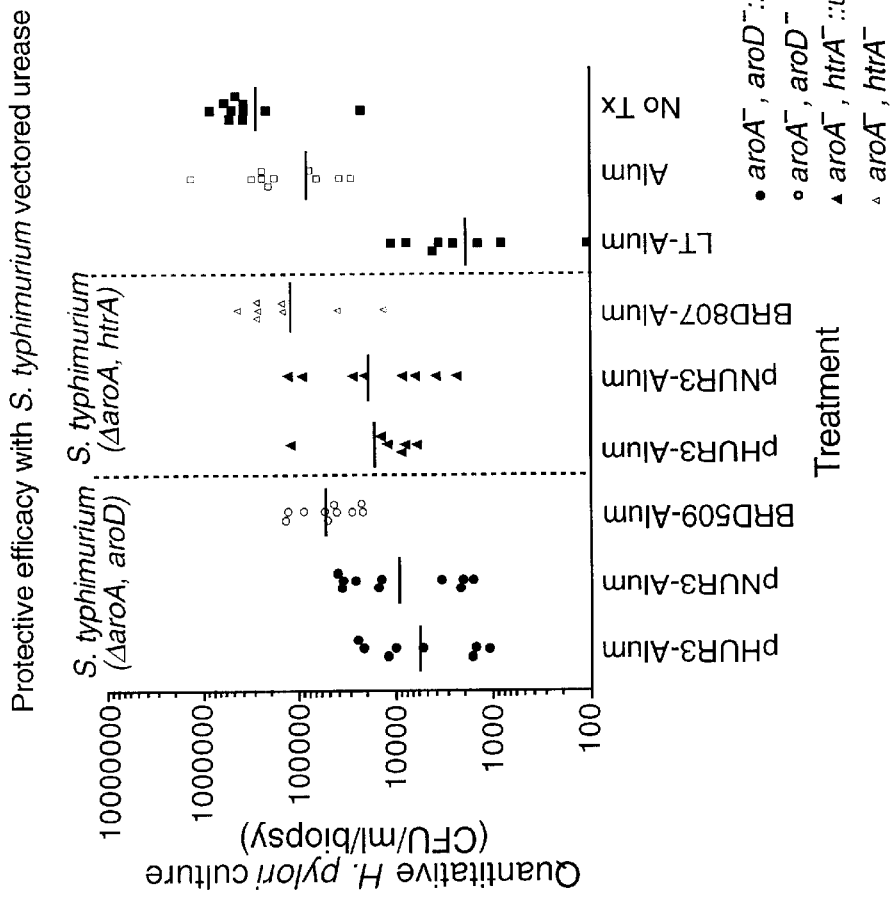
FIG. 3A is a graph showing protection against Helicobacter infection in mice that were mucosally primed with *S. typhimurium*-vectored urease, followed by parenteral boosting with urease and alum.

The level of protective efficacy employing *S. typhimurium*-vectored urease in a prime-boost strategy was determined. FIG. 3A shows the results of quantitative *H. pylori* culture of mice immunized on day 0 with 1E10 CFU/ml live attenuated *S. typhimurium* (ΔaroA/ΔaroD or ΔaroA/ΔhtrA) and boosted on days 21 and 35 with urease (10 μg) plus alum (200 μg). Three weeks later, animals were challenged with *H. pylori* (1E7 CFU/ml) and efficacy was assessed in gastric tissue 4 weeks later using quantitative culture. Strains including the urease constructs are indicated in the key of FIG. 3A. FIG. 3B shows protection depicted as $\log_{10}$ reduction in comparison to the no treatment (Tx) control group. A significant reduction in bacterial burden was observed when attenuated Salmonella expressing urease was administered as part of a prime-boost regimen with alum (Wilcoxon rank sum compared to parental control strain). No significant difference was observed between group 1 (pHUR3-Alum) and group 7 (LT-Alum).

All patents and publications cited above are hereby incorporated by reference in their entirety.

SEQUENCE LISTING

```
<160> NUMBER OF SEQ ID NOS: 52

<210> SEQ ID NO 1
<211> LENGTH: 4824
<212> TYPE: DNA
<213> ORGANISM: Artificial Sequence
<220> FEATURE:
<223> OTHER INFORMATION: includes sequences from Helicobacter pylori,
      Salmonella typhimurium, and Escherichia coli
<221> NAME/KEY: CDS
<222> LOCATION: (2)...(31)
<221> NAME/KEY: CDS
<222> LOCATION: (41)...(61)
<221> NAME/KEY: CDS
<222> LOCATION: (65)...(799)
<221> NAME/KEY: CDS
<222> LOCATION: (803)...(2512)
<221> NAME/KEY: CDS
<222> LOCATION: (2516)...(2692)
<221> NAME/KEY: CDS
<222> LOCATION: (2696)...(2896)
<221> NAME/KEY: CDS
<222> LOCATION: (2900)...(3322)
<221> NAME/KEY: CDS
<222> LOCATION: (3326)...(3385)
<221> NAME/KEY: CDS
<222> LOCATION: (3389)...(3406)
<221> NAME/KEY: CDS
<222> LOCATION: (3410)...(3466)
<221> NAME/KEY: CDS
<222> LOCATION: (3470)...(3598)
<221> NAME/KEY: CDS
<222> LOCATION: (3602)...(3661)
<221> NAME/KEY: CDS
<222> LOCATION: (3665)...(3697)
<221> NAME/KEY: CDS
<222> LOCATION: (3701)...(3769)
<221> NAME/KEY: CDS
<222> LOCATION: (3773)...(3817)
<221> NAME/KEY: CDS
<222> LOCATION: (3821)...(3844)
<221> NAME/KEY: CDS
```

<222> LOCATION: (3848)...(3889)

<400> SEQUENCE: 1

| | |
|---|---:|
| g aat tct att ccg gaa ctt cgc gtt ata aaa tgaatctga cgt aca cag<br>  Asn Ser Ile Pro Glu Leu Arg Val Ile Lys        Arg Thr Gln<br>   1            5              10 | 49 |
| caa ttt aga tat taa tca tcc aca gga gag atc tcc atg aaa ctc acc<br>Gln Phe Arg Tyr     Ser Ser Thr Gly Glu Ile Ser Met Lys Leu Thr<br>     15               20              25 | 97 |
| cca aaa gag tta gat aag ttg atg ctc cac tac gct gga gaa ttg gct<br>Pro Lys Glu Leu Asp Lys Leu Met Leu His Tyr Ala Gly Glu Leu Ala<br> 30                35              40 | 145 |
| aaa aaa cgc aaa gaa aaa ggc att aag ctt aac tat gta gaa gca gta<br>Lys Lys Arg Lys Glu Lys Gly Ile Lys Leu Asn Tyr Val Glu Ala Val<br>     45               50              55              60 | 193 |
| gct ttg att agt gcc cat att atg gaa gaa gcg aga gct ggt aaa aag<br>Ala Leu Ile Ser Ala His Ile Met Glu Glu Ala Arg Ala Gly Lys Lys<br>             65                70              75 | 241 |
| act gcg gct gaa ttg atg caa gaa ggg cgc act ctt tta aaa cca gat<br>Thr Ala Ala Glu Leu Met Gln Glu Gly Arg Thr Leu Leu Lys Pro Asp<br>  80                85              90 | 289 |
| gat gtg atg gat ggc gtg gca agc atg atc cat gaa gtg ggt att gaa<br>Asp Val Met Asp Gly Val Ala Ser Met Ile His Glu Val Gly Ile Glu<br>         95               100           105 | 337 |
| gcg atg ttt cct gat ggg act aaa ctc gta acc gtg cat acc cct att<br>Ala Met Phe Pro Asp Gly Thr Lys Leu Val Thr Val His Thr Pro Ile<br>110                115              120 | 385 |
| gag gcc aat ggt aaa tta gtt cct ggt gag ttg ttc tta aaa aat gaa<br>Glu Ala Asn Gly Lys Leu Val Pro Gly Glu Leu Phe Leu Lys Asn Glu<br>125                130              135              140 | 433 |
| gac atc act atc aac gaa ggc aaa aaa gcc gtt agc gtg aaa gtt aaa<br>Asp Ile Thr Ile Asn Glu Gly Lys Lys Ala Val Ser Val Lys Val Lys<br>                145              150              155 | 481 |
| aat gtt ggc gac aga ccg gtt caa atc ggc tca cac ttc cat ttc ttt<br>Asn Val Gly Asp Arg Pro Val Gln Ile Gly Ser His Phe His Phe Phe<br>                    160              165              170 | 529 |
| gaa gtg aat aga tgc cta gac ttt gac aga gaa aaa act ttc ggt aaa<br>Glu Val Asn Arg Cys Leu Asp Phe Asp Arg Glu Lys Thr Phe Gly Lys<br>              175              180              185 | 577 |
| cgc tta gac att gcg agc ggg aca gcg gta aga ttt gag cct ggc gaa<br>Arg Leu Asp Ile Ala Ser Gly Thr Ala Val Arg Phe Glu Pro Gly Glu<br>           190                195              200 | 625 |
| gaa aaa tcc gta gaa ttg att gac att ggc ggt aac aga aga atc ttt<br>Glu Lys Ser Val Glu Leu Ile Asp Ile Gly Gly Asn Arg Arg Ile Phe<br>205                210              215              220 | 673 |
| gga ttt aac gca ttg gtt gat aga caa gca gac aac gaa agc aaa aaa<br>Gly Phe Asn Ala Leu Val Asp Arg Gln Ala Asp Asn Glu Ser Lys Lys<br>                225              230              235 | 721 |
| att gct tta cac aga gct aaa gag cgt ggt ttt cat ggc gct aaa agc<br>Ile Ala Leu His Arg Ala Lys Glu Arg Gly Phe His Gly Ala Lys Ser<br>              240              245              250 | 769 |
| gat gac aac tat gta aaa aca att aag gag taa gaa atg aaa aag att<br>Asp Asp Asn Tyr Val Lys Thr Ile Lys Glu     Glu Met Lys Lys Ile<br>          255              260                       265 | 817 |
| agc aga aaa gaa tat gtt tct atg tat ggt cct act aca ggc gat aaa<br>Ser Arg Lys Glu Tyr Val Ser Met Tyr Gly Pro Thr Thr Gly Asp Lys<br>        270                275              280 | 865 |
| gtg aga ttg ggc gat aca gac ttg atc gct gaa gta gaa cat gac tac<br>Val Arg Leu Gly Asp Thr Asp Leu Ile Ala Glu Val Glu His Asp Tyr<br>285                290              295 | 913 |

```
acc att tat ggc gaa gag ctt aaa ttc ggt ggc ggt aaa acc cta aga         961
Thr Ile Tyr Gly Glu Glu Leu Lys Phe Gly Gly Gly Lys Thr Leu Arg
300                 305                 310                 315 gaa ggc atg agc caa tct aac aac cct agc aaa gaa gag ttg gat tta        1009
Glu Gly Met Ser Gln Ser Asn Asn Pro Ser Lys Glu Glu Leu Asp Leu
                320                 325                 330 att atc act aac gct tta atc gtg gat tac acc ggt att tat aaa gcg        1057
Ile Ile Thr Asn Ala Leu Ile Val Asp Tyr Thr Gly Ile Tyr Lys Ala
            335                 340                 345 gat att ggt att aaa gat ggc aaa atc gct ggc att ggt aaa ggc ggt        1105
Asp Ile Gly Ile Lys Asp Gly Lys Ile Ala Gly Ile Gly Lys Gly Gly
        350                 355                 360 aac aaa gac atg caa gat ggc gtt aaa aac aat ctt agc gta ggt cct        1153
Asn Lys Asp Met Gln Asp Gly Val Lys Asn Asn Leu Ser Val Gly Pro
    365                 370                 375 gct act gaa gcc tta gcc ggt gaa ggt ttg atc gta acg gct ggt ggt        1201
Ala Thr Glu Ala Leu Ala Gly Glu Gly Leu Ile Val Thr Ala Gly Gly
380                 385                 390                 395 att gac aca cac atc cac ttc att tca ccc caa caa atc cct aca gct        1249
Ile Asp Thr His Ile His Phe Ile Ser Pro Gln Gln Ile Pro Thr Ala
                400                 405                 410 ttt gca agc ggt gta aca acc atg att ggt ggt gga acc ggt cct gct        1297
Phe Ala Ser Gly Val Thr Thr Met Ile Gly Gly Gly Thr Gly Pro Ala
            415                 420                 425 gat ggc act aat gcg act act atc act cca ggc aga aga aat tta aaa        1345
Asp Gly Thr Asn Ala Thr Thr Ile Thr Pro Gly Arg Arg Asn Leu Lys
        430                 435                 440 tgg atg ctc aga gcg gct gaa gaa tat tct atg aat tta ggt ttc ttg        1393
Trp Met Leu Arg Ala Ala Glu Glu Tyr Ser Met Asn Leu Gly Phe Leu
    445                 450                 455 gct aaa ggt aac gct tct aac gat gcg agc tta gcc gat caa att gaa        1441
Ala Lys Gly Asn Ala Ser Asn Asp Ala Ser Leu Ala Asp Gln Ile Glu
460                 465                 470                 475 gcc ggt gcg att ggc ttt gca att cac gaa gac tgg ggc acc act cct        1489
Ala Gly Ala Ile Gly Phe Ala Ile His Glu Asp Trp Gly Thr Thr Pro
                480                 485                 490 tct gca atc aat cat gcg tta gat gtt gcg gac aaa tac gat gtg caa        1537
Ser Ala Ile Asn His Ala Leu Asp Val Ala Asp Lys Tyr Asp Val Gln
            495                 500                 505 gtc gct atc gcc aca gac act ttg aat gaa gcc ggt tgt gta gaa gac        1585
Val Ala Ile Ala Thr Asp Thr Leu Asn Glu Ala Gly Cys Val Glu Asp
        510                 515                 520 act atg gct gct att gct gga cgc act atg cac act ttc cac act gaa        1633
Thr Met Ala Ala Ile Ala Gly Arg Thr Met His Thr Phe His Thr Glu
    525                 530                 535 ggc gct ggc ggc gga cac gct cct gat att att aaa gta gcc ggt gaa        1681
Gly Ala Gly Gly Gly His Ala Pro Asp Ile Ile Lys Val Ala Gly Glu
540                 545                 550                 555 cac aac att ctt ccc gct tcc act aac ccc acc atc cct ttc acc gtg        1729
His Asn Ile Leu Pro Ala Ser Thr Asn Pro Thr Ile Pro Phe Thr Val
                560                 565                 570 aat aca gaa gca gag cac atg gac atg ctt atg gtg tgc cac cac ttg        1777
Asn Thr Glu Ala Glu His Met Asp Met Leu Met Val Cys His His Leu
            575                 580                 585 gat aaa agc att aaa gaa gat gtt cag ttc gct gat tca agg atc cgc        1825
Asp Lys Ser Ile Lys Glu Asp Val Gln Phe Ala Asp Ser Arg Ile Arg
        590                 595                 600 cct caa acc att gcg gct gaa gac act ttg cat gac atg ggg att ttc        1873
Pro Gln Thr Ile Ala Ala Glu Asp Thr Leu His Asp Met Gly Ile Phe
```

```
                605                 610                 615
tca atc acc agt tct gac tct caa gcg atg ggc cgt gtg ggt gaa gtt    1921
Ser Ile Thr Ser Ser Asp Ser Gln Ala Met Gly Arg Val Gly Glu Val
620                 625                 630                 635 atc act aga act tgg caa aca gct gac aaa aac aag aaa gaa ttt ggc    1969
Ile Thr Arg Thr Trp Gln Thr Ala Asp Lys Asn Lys Lys Glu Phe Gly
                640                 645                 650 cgc ttg aaa gaa gaa aaa ggc gat aac gac aac ttc agg atc aaa cgc    2017
Arg Leu Lys Glu Glu Lys Gly Asp Asn Asp Asn Phe Arg Ile Lys Arg
            655                 660                 665 tac ttg tct aaa tac acc att aac cca gcg atc gct cat ggg att agc    2065
Tyr Leu Ser Lys Tyr Thr Ile Asn Pro Ala Ile Ala His Gly Ile Ser
        670                 675                 680 gag tat gta ggt tca gta gaa gtg ggc aaa gtg gct gac ttg gta ttg    2113
Glu Tyr Val Gly Ser Val Glu Val Gly Lys Val Ala Asp Leu Val Leu
    685                 690                 695 tgg agt cca gca ttc ttt ggc gtg aaa ccc aac atg atc atc aaa ggc    2161
Trp Ser Pro Ala Phe Phe Gly Val Lys Pro Asn Met Ile Ile Lys Gly
700                 705                 710                 715 gga ttc att gcg tta agc caa atg ggc gat gcg aac gct tct atc cct    2209
Gly Phe Ile Ala Leu Ser Gln Met Gly Asp Ala Asn Ala Ser Ile Pro
                720                 725                 730 acc cca caa ccg gtt tat tac aga gaa atg ttc gct cat cat ggt aaa    2257
Thr Pro Gln Pro Val Tyr Tyr Arg Glu Met Phe Ala His His Gly Lys
            735                 740                 745 gct aaa tac gat gca aac atc act ttt gtg tct caa gcg gct tat gac    2305
Ala Lys Tyr Asp Ala Asn Ile Thr Phe Val Ser Gln Ala Ala Tyr Asp
        750                 755                 760 aaa ggc att aaa gaa gaa tta gga ctt gaa aga caa gtg ttg ccg gta    2353
Lys Gly Ile Lys Glu Glu Leu Gly Leu Glu Arg Gln Val Leu Pro Val
    765                 770                 775 aaa aat tgc aga aat atc act aaa aaa gac atg caa ttc aac gac act    2401
Lys Asn Cys Arg Asn Ile Thr Lys Lys Asp Met Gln Phe Asn Asp Thr
780                 785                 790                 795 acc gct cac att gaa gtc aat cct gaa act tac cat gtg ttc gtg gat    2449
Thr Ala His Ile Glu Val Asn Pro Glu Thr Tyr His Val Phe Val Asp
                800                 805                 810 ggc aaa gaa gta act tct aaa cca gcc aat aaa gtg agc ttg gcg caa    2497
Gly Lys Glu Val Thr Ser Lys Pro Ala Asn Lys Val Ser Leu Ala Gln
            815                 820                 825 ctc ttt agc att ttc tag gat ttt tta gga gca acg ctc ctt aga tcc    2545
Leu Phe Ser Ile Phe     Asp Phe Leu Gly Ala Thr Leu Leu Arg Ser
        830                     835                 840 ccg gga att ggg gat ccg cta gcc cgc cta atg agc ggg ctt ttt ttt    2593
Pro Gly Ile Gly Asp Pro Leu Ala Arg Leu Met Ser Gly Leu Phe Phe
    845                 850                 855 ctc ggg cag cgt tgg gtc ctg gcc acg ggt gcg cat gat cgt gct cct    2641
Leu Gly Gln Arg Trp Val Leu Ala Thr Gly Ala His Asp Arg Ala Pro
860                 865                 870 gtc gtt gag gac ccg gct agg ctg gcg ggg ttg cct tac tgg tta gca    2689
Val Val Glu Asp Pro Ala Arg Leu Ala Gly Leu Pro Tyr Trp Leu Ala
875                 880                 885                 890 gaa tga atc acc gat acg cga gcg aac gtg aag cga ctg ctg ctg caa    2737
Glu     Ile Thr Asp Thr Arg Ala Asn Val Lys Arg Leu Leu Leu Gln
                895                 900                 905 aac gtc tgc gac ctg agc aac aac atg aat ggt ctt cgg ttt ccg tgt    2785
Asn Val Cys Asp Leu Ser Asn Asn Met Asn Gly Leu Arg Phe Pro Cys
            910                 915                 920 ttc gta aag tct gga aac gcg gaa gtc agc gct ctt ccg ctt cct cgc    2833
```

```
                Phe Val Lys Ser Gly Asn Ala Glu Val Ser Ala Leu Pro Leu Pro Arg
                            925                 930                 935 tca ctg act cgc tgc gct cgg tcg ttc ggc tgc ggc gag cgg tat cag        2881
Ser Leu Thr Arg Cys Ala Arg Ser Phe Gly Cys Gly Glu Arg Tyr Gln
            940                 945                 950 ctc act caa agg cgg taa tac ggt tat cca cag aat cag gga ata acg        2929
Leu Thr Gln Arg Arg     Tyr Gly Tyr Pro Gln Asn Gln Gly Ile Thr
        955                     960                 965 cag gaa aga aca tgt gag caa aag gcc agc aaa agg cca gga acc gta        2977
Gln Glu Arg Thr Cys Glu Gln Lys Ala Ser Lys Arg Pro Gly Thr Val
        970                 975                 980 aaa agg ccg cgt tgc tgg cgt ttt tcc ata ggc tcc gcc ccc ctg acg        3025
Lys Arg Pro Arg Cys Trp Arg Phe Ser Ile Gly Ser Ala Pro Leu Thr
    985                 990                 995                 1000 agc atc aca aaa atc gac gct caa gtc aga ggt ggc gaa acc cga cag        3073
Ser Ile Thr Lys Ile Asp Ala Gln Val Arg Gly Gly Glu Thr Arg Gln
            1005                1010                1015 gac tat aaa gat acc agg cgt ttc ccc ctg gaa gct ccc tcg tgc gct        3121
Asp Tyr Lys Asp Thr Arg Arg Phe Pro Leu Glu Ala Pro Ser Cys Ala
            1020                1025                1030 ctc ctg ttc cga ccc tgc cgc tta ccg gat acc tgt ccg cct ttc tcc        3169
Leu Leu Phe Arg Pro Cys Arg Leu Pro Asp Thr Cys Pro Pro Phe Ser
        1035                1040                1045 ctt cgg gaa gcg tgg cgc ttt ctc aat gct cac gct gta ggt atc tca        3217
Leu Arg Glu Ala Trp Arg Phe Leu Asn Ala His Ala Val Gly Ile Ser
        1050                1055                1060 gtt cgg tgt agg tcg ttc gct cca agc tgg gct gtg tgc acg aac ccc        3265
Val Arg Cys Arg Ser Phe Ala Pro Ser Trp Ala Val Cys Thr Asn Pro
1065                1070                1075                1080 ccg ttc agc ccg acc gct gcg cct tat ccg gta act atc gtc ttg agt        3313
Pro Phe Ser Pro Thr Ala Ala Pro Tyr Pro Val Thr Ile Val Leu Ser
            1085                1090                1095 cca acc cgg taa gac acg act tat cgc cac tgg cag cag cca ctg gta        3361
Pro Thr Arg     Asp Thr Thr Tyr Arg His Trp Gln Gln Pro Leu Val
                    1100                1105                1110 aca gga tta gca gag cga ggt atg tag gcg gtg cta cag agt tct            3406
Thr Gly Leu Ala Glu Arg Gly Met     Ala Val Leu Gln Ser Ser
        1115                1120                1125 tga agt ggt ggc cta act acg gct aca cta gaa gga cag tat ttg gta        3454
    Ser Gly Gly Leu Thr Thr Ala Thr Leu Glu Gly Gln Tyr Leu Val
            1130                1135                1140 tct gcg ctc tgc tga agc cag tta cct tcg gaa aaa gag ttg gta gct        3502
Ser Ala Leu Cys     Ser Gln Leu Pro Ser Glu Lys Glu Leu Val Ala
                    1145                1150                1155 ctt gat ccg gca aac aaa cca ccg ctg gta gcg gtg gtt ttt ttg ttt        3550
Leu Asp Pro Ala Asn Lys Pro Pro Leu Val Ala Val Phe Leu Phe
                1160                1165                1170 gca agc agc aga tta cgc gca gaa aaa aag gat ctc aag aag atc ctt        3598
Ala Ser Ser Arg Leu Arg Ala Glu Lys Lys Asp Leu Lys Lys Ile Leu
            1175                1180                1185 tga tct ttt cta cgg ggt ctg acg ctc agt gga acg aaa act cac gtt        3646
    Ser Phe Leu Arg Gly Leu Thr Leu Ser Gly Thr Lys Thr His Val
            1190                1195                1200 aag gga ttt tgg tca tga gat tat caa aaa gga tct tca cct aga tcc        3694
Lys Gly Phe Trp Ser     Asp Tyr Gln Lys Gly Ser Ser Pro Arg Ser
        1205                    1210                1215 ttt taa att aaa aat gaa gtt tta aat caa tct aaa gta tat atg agt        3742
Phe     Ile Lys Asn Glu Val Leu Asn Gln Ser Lys Val Tyr Met Ser
            1220                1225                1230
```

```
aaa ctt ggt ctg aca gtt acc aat gct taa tca gtg agg cac cta tct      3790
Lys Leu Gly Leu Thr Val Thr Asn Ala     Ser Val Arg His Leu Ser
        1235                1240                1245 cag cga tct gtc tat ttc gtt cat cca tag ttg cct gac tcc ccg tcg      3838
Gln Arg Ser Val Tyr Phe Val His Pro     Leu Pro Asp Ser Pro Ser
        1250                1255                1260 tgt aga taa cta cga tac ggg agg gct tac cat ctg gcc cca gtg ctg      3886
Cys Arg     Leu Arg Tyr Gly Arg Ala Tyr His Leu Ala Pro Val Leu
                1265                1270                1275 caa tgataccgcg agacccacgc tcaccggctc cagatttatc agcaataaac            3939
Gln cagccagccg aagggccga gcgcagaagt ggtcctgcaa ctttatccgc ctccatccag      3999
tctattaatt gttgccggga agctagagta agtagttcgc cagttaatag tttgcgcaac    4059
gttgttgcca ttgctgcagg catcgtggtg tcacgctcgt cgtttggtat ggcttcattc    4119
agctccggtt cccaacgatc aaggcgagtt acatgatccc ccatgttgtg caaaaaagcg    4179
gttagctcct tcggtcctcc gatcgttgtc agaagtaagt tggccgcagt gttatcactc    4239
atggttatgg cagcactgca taattctctt actgtcatgc catccgtaag atgcttttct    4299
gtgactggtg agtactcaac caagtcattc tgagaatagt gtatgcggcg accgagttgc    4359
tcttgcccgg cgtcaacacg ggataatacc gcgccacata gcagaacttt aaaagtgctc    4419
atcattggaa aacgttcttc ggggcgaaaa ctctcaagga tcttaccgct gttgagatcc    4479
agttcgatgt aacccactcg tgcacccaac tgatcttcag catctttttac tttcaccagc   4539 gtttctgggt gagcaaaaac aggaaggcaa aatgccgcaa aaagggaat aagggcgaca     4599 cggaaatgtt gaatactcat actcttcctt tttcaatatt attgaagcat ttatcagggt    4659
tattgtctca tgagcggata catatttgaa tgtatttaga aaaataaaca aatagggggtt   4719 ccgcgcacat ttccccgaaa agtgccacct gacgtctaag aaaccattat tatcatgaca    4779
ttaacctata aaaataggcg tatcacgagg cccttttcgtc ttcaa                   4824
```

<210> SEQ ID NO 2
<211> LENGTH: 10
<212> TYPE: PRT
<213> ORGANISM: Salmonella typhimurium

<400> SEQUENCE: 2

Asn Ser Ile Pro Glu Leu Arg Val Ile Lys
1               5                   10

<210> SEQ ID NO 3
<211> LENGTH: 7
<212> TYPE: PRT
<213> ORGANISM: Salmonella typhimurium

<400> SEQUENCE: 3

Arg Thr Gln Gln Phe Arg Tyr
1               5

<210> SEQ ID NO 4
<211> LENGTH: 245
<212> TYPE: PRT
<213> ORGANISM: Artificial Sequence
<220> FEATURE:
<223> OTHER INFORMATION: includes sequences from Salmonella
      typhimurium and Helicobacter pylori.

<400> SEQUENCE: 4

Ser Ser Thr Gly Glu Ile Ser Met Lys Leu Thr Pro Lys Glu Leu Asp

-continued

```
               1               5                  10                 15
Lys Leu Met Leu His Tyr Ala Gly Glu Leu Ala Lys Lys Arg Lys Glu
                        20                  25                  30
Lys Gly Ile Lys Leu Asn Tyr Val Glu Ala Val Ala Leu Ile Ser Ala
                35                  40                  45
His Ile Met Glu Glu Ala Arg Ala Gly Lys Lys Thr Ala Ala Glu Leu
         50                  55                  60
Met Gln Glu Gly Arg Thr Leu Leu Lys Pro Asp Asp Val Met Asp Gly
 65                  70                  75                  80
Val Ala Ser Met Ile His Glu Val Gly Ile Glu Ala Met Phe Pro Asp
                    85                  90                  95
Gly Thr Lys Leu Val Thr Val His Thr Pro Ile Glu Ala Asn Gly Lys
                100                 105                 110
Leu Val Pro Gly Glu Leu Phe Leu Lys Asn Glu Asp Ile Thr Ile Asn
            115                 120                 125
Glu Gly Lys Lys Ala Val Ser Val Lys Val Lys Asn Val Gly Asp Arg
        130                 135                 140
Pro Val Gln Ile Gly Ser His Phe His Phe Phe Glu Val Asn Arg Cys
145                 150                 155                 160
Leu Asp Phe Asp Arg Glu Lys Thr Phe Gly Lys Arg Leu Asp Ile Ala
                165                 170                 175
Ser Gly Thr Ala Val Arg Phe Glu Pro Gly Glu Glu Lys Ser Val Glu
                180                 185                 190
Leu Ile Asp Ile Gly Gly Asn Arg Arg Ile Phe Gly Phe Asn Ala Leu
            195                 200                 205
Val Asp Arg Gln Ala Asp Asn Glu Ser Lys Lys Ile Ala Leu His Arg
        210                 215                 220
Ala Lys Glu Arg Gly Phe His Gly Ala Lys Ser Asp Asp Asn Tyr Val
225                 230                 235                 240
Lys Thr Ile Lys Glu
                245

<210> SEQ ID NO 5
<211> LENGTH: 570
<212> TYPE: PRT
<213> ORGANISM: Helicobacter pylori

<400> SEQUENCE: 5

Glu Met Lys Lys Ile Ser Arg Lys Glu Tyr Val Ser Met Tyr Gly Pro
 1               5                  10                 15
Thr Thr Gly Asp Lys Val Arg Leu Gly Asp Thr Asp Leu Ile Ala Glu
                20                  25                  30
Val Glu His Asp Tyr Thr Ile Tyr Gly Glu Glu Leu Lys Phe Gly Gly
            35                  40                  45
Gly Lys Thr Leu Arg Glu Gly Met Ser Gln Ser Asn Asn Pro Ser Lys
        50                  55                  60
Glu Glu Leu Asp Leu Ile Ile Thr Asn Ala Leu Ile Val Asp Tyr Thr
 65                  70                  75                  80
Gly Ile Tyr Lys Ala Asp Ile Gly Ile Lys Asp Gly Lys Ile Ala Gly
                    85                  90                  95
Ile Gly Lys Gly Gly Asn Lys Asp Met Gln Asp Gly Val Lys Asn Asn
                100                 105                 110
Leu Ser Val Gly Pro Ala Thr Glu Ala Leu Ala Gly Glu Gly Leu Ile
            115                 120                 125
```

-continued

```
Val Thr Ala Gly Gly Ile Asp Thr His Ile His Phe Ile Ser Pro Gln
    130                 135                 140

Gln Ile Pro Thr Ala Phe Ala Ser Gly Val Thr Thr Met Ile Gly Gly
145                 150                 155                 160

Gly Thr Gly Pro Ala Asp Gly Thr Asn Ala Thr Thr Ile Thr Pro Gly
                165                 170                 175

Arg Arg Asn Leu Lys Trp Met Leu Arg Ala Ala Glu Glu Tyr Ser Met
        180                 185                 190

Asn Leu Gly Phe Leu Ala Lys Gly Asn Ala Ser Asn Asp Ala Ser Leu
            195                 200                 205

Ala Asp Gln Ile Glu Ala Gly Ala Ile Gly Phe Ala Ile His Glu Asp
    210                 215                 220

Trp Gly Thr Thr Pro Ser Ala Ile Asn His Ala Leu Asp Val Ala Asp
225                 230                 235                 240

Lys Tyr Asp Val Gln Val Ala Ile Ala Thr Asp Thr Leu Asn Glu Ala
                245                 250                 255

Gly Cys Val Glu Asp Thr Met Ala Ala Ile Ala Gly Arg Thr Met His
        260                 265                 270

Thr Phe His Thr Glu Gly Ala Gly Gly His Ala Pro Asp Ile Ile
            275                 280                 285

Lys Val Ala Gly Glu His Asn Ile Leu Pro Ala Ser Thr Asn Pro Thr
    290                 295                 300

Ile Pro Phe Thr Val Asn Thr Glu Ala Glu His Met Asp Met Leu Met
305                 310                 315                 320

Val Cys His His Leu Asp Lys Ser Ile Lys Glu Asp Val Gln Phe Ala
                325                 330                 335

Asp Ser Arg Ile Arg Pro Gln Thr Ile Ala Ala Glu Asp Thr Leu His
        340                 345                 350

Asp Met Gly Ile Phe Ser Ile Thr Ser Ser Asp Ser Gln Ala Met Gly
            355                 360                 365

Arg Val Gly Glu Val Ile Thr Arg Thr Trp Gln Thr Ala Asp Lys Asn
    370                 375                 380

Lys Lys Glu Phe Gly Arg Leu Lys Glu Glu Lys Gly Asp Asn Asp Asn
385                 390                 395                 400

Phe Arg Ile Lys Arg Tyr Leu Ser Lys Tyr Thr Ile Asn Pro Ala Ile
                405                 410                 415

Ala His Gly Ile Ser Glu Tyr Val Gly Ser Val Glu Val Gly Lys Val
        420                 425                 430

Ala Asp Leu Val Leu Trp Ser Pro Ala Phe Phe Gly Val Lys Pro Asn
            435                 440                 445

Met Ile Ile Lys Gly Gly Phe Ile Ala Leu Ser Gln Met Gly Asp Ala
    450                 455                 460

Asn Ala Ser Ile Pro Thr Pro Gln Pro Val Tyr Tyr Arg Glu Met Phe
465                 470                 475                 480

Ala His His Gly Lys Ala Lys Tyr Asp Ala Asn Ile Thr Phe Val Ser
                485                 490                 495

Gln Ala Ala Tyr Asp Lys Gly Ile Lys Glu Glu Leu Gly Leu Glu Arg
        500                 505                 510

Gln Val Leu Pro Val Lys Asn Cys Arg Asn Ile Thr Lys Lys Asp Met
            515                 520                 525

Gln Phe Asn Asp Thr Thr Ala His Ile Glu Val Asn Pro Glu Thr Tyr
    530                 535                 540

His Val Phe Val Asp Gly Lys Glu Val Thr Ser Lys Pro Ala Asn Lys
```

```
545                 550                 555                 560
Val Ser Leu Ala Gln Leu Phe Ser Ile Phe
                565                 570

<210> SEQ ID NO 6
<211> LENGTH: 59
<212> TYPE: PRT
<213> ORGANISM: Salmonella typhimurium

<400> SEQUENCE: 6

Asp Phe Leu Gly Ala Thr Leu Leu Arg Ser Pro Gly Ile Gly Asp Pro
 1               5                  10                  15

Leu Ala Arg Leu Met Ser Gly Leu Phe Phe Leu Gly Gln Arg Trp Val
            20                  25                  30

Leu Ala Thr Gly Ala His Asp Arg Ala Pro Val Val Glu Asp Pro Ala
        35                  40                  45

Arg Leu Ala Gly Leu Pro Tyr Trp Leu Ala Glu
    50                  55

<210> SEQ ID NO 7
<211> LENGTH: 67
<212> TYPE: PRT
<213> ORGANISM: Salmonella typhimurium

<400> SEQUENCE: 7

Ile Thr Asp Thr Arg Ala Asn Val Lys Arg Leu Leu Leu Gln Asn Val
 1               5                  10                  15

Cys Asp Leu Ser Asn Asn Met Asn Gly Leu Arg Phe Pro Cys Phe Val
            20                  25                  30

Lys Ser Gly Asn Ala Glu Val Ser Ala Leu Pro Leu Pro Arg Ser Leu
        35                  40                  45

Thr Arg Cys Ala Arg Ser Phe Gly Cys Gly Glu Arg Tyr Gln Leu Thr
    50                  55                  60

Gln Arg Arg
65

<210> SEQ ID NO 8
<211> LENGTH: 141
<212> TYPE: PRT
<213> ORGANISM: Salmonella typhimurium

<400> SEQUENCE: 8

Tyr Gly Tyr Pro Gln Asn Gly Ile Thr Gln Glu Arg Thr Cys Glu
 1               5                  10                  15

Gln Lys Ala Ser Lys Arg Pro Gly Thr Val Lys Arg Pro Arg Cys Trp
            20                  25                  30

Arg Phe Ser Ile Gly Ser Ala Pro Leu Thr Ser Ile Thr Lys Ile Asp
        35                  40                  45

Ala Gln Val Arg Gly Gly Glu Thr Arg Gln Asp Tyr Lys Asp Thr Arg
    50                  55                  60

Arg Phe Pro Leu Glu Ala Pro Ser Cys Ala Leu Leu Phe Arg Pro Cys
65                  70                  75                  80

Arg Leu Pro Asp Thr Cys Pro Pro Phe Ser Leu Arg Glu Ala Trp Arg
                85                  90                  95

Phe Leu Asn Ala His Ala Val Gly Ile Ser Val Arg Cys Arg Ser Phe
            100                 105                 110

Ala Pro Ser Trp Ala Val Cys Thr Asn Pro Pro Phe Ser Pro Thr Ala
        115                 120                 125
```

```
Ala Pro Tyr Pro Val Thr Ile Val Leu Ser Pro Thr Arg
    130                 135                 140
```

<210> SEQ ID NO 9
<211> LENGTH: 20
<212> TYPE: PRT
<213> ORGANISM: Salmonella typhimurium

<400> SEQUENCE: 9

```
Asp Thr Thr Tyr Arg His Trp Gln Gln Pro Leu Val Thr Gly Leu Ala
 1               5                  10                  15

Glu Arg Gly Met
            20
```

<210> SEQ ID NO 10
<211> LENGTH: 6
<212> TYPE: PRT
<213> ORGANISM: Salmonella typhimurium

<400> SEQUENCE: 10

```
Ala Val Leu Gln Ser Ser
 1               5
```

<210> SEQ ID NO 11
<211> LENGTH: 19
<212> TYPE: PRT
<213> ORGANISM: Salmonella typhimurium

<400> SEQUENCE: 11

```
Ser Gly Gly Leu Thr Thr Ala Thr Leu Glu Gly Gln Tyr Leu Val Ser
 1               5                  10                  15

Ala Leu Cys
```

<210> SEQ ID NO 12
<211> LENGTH: 43
<212> TYPE: PRT
<213> ORGANISM: Salmonella typhimurium

<400> SEQUENCE: 12

```
Ser Gln Leu Pro Ser Glu Lys Glu Leu Val Ala Leu Asp Pro Ala Asn
 1               5                  10                  15

Lys Pro Pro Leu Val Ala Val Val Phe Leu Phe Ala Ser Ser Arg Leu
                20                  25                  30

Arg Ala Glu Lys Lys Asp Leu Lys Lys Ile Leu
            35                  40
```

<210> SEQ ID NO 13
<211> LENGTH: 20
<212> TYPE: PRT
<213> ORGANISM: Salmonella typhimurium

<400> SEQUENCE: 13

```
Ser Phe Leu Arg Gly Leu Thr Leu Ser Gly Thr Lys Thr His Val Lys
 1               5                  10                  15

Gly Phe Trp Ser
            20
```

<210> SEQ ID NO 14
<211> LENGTH: 11
<212> TYPE: PRT
<213> ORGANISM: Salmonella typhimurium

```
-continued

<400> SEQUENCE: 14

Asp Tyr Gln Lys Gly Ser Ser Pro Arg Ser Phe
1               5                   10

<210> SEQ ID NO 15
<211> LENGTH: 23
<212> TYPE: PRT
<213> ORGANISM: Salmonella typhimurium

<400> SEQUENCE: 15

Ile Lys Asn Glu Val Leu Asn Gln Ser Lys Val Tyr Met Ser Lys Leu
1               5                   10                  15

Gly Leu Thr Val Thr Asn Ala
            20

<210> SEQ ID NO 16
<211> LENGTH: 15
<212> TYPE: PRT
<213> ORGANISM: Salmonella typhimurium

<400> SEQUENCE: 16

Ser Val Arg His Leu Ser Gln Arg Ser Val Tyr Phe Val His Pro
1               5                   10                  15

<210> SEQ ID NO 17
<211> LENGTH: 8
<212> TYPE: PRT
<213> ORGANISM: Salmonella typhimurium

<400> SEQUENCE: 17

Leu Pro Asp Ser Pro Ser Cys Arg
1               5

<210> SEQ ID NO 18
<211> LENGTH: 14
<212> TYPE: PRT
<213> ORGANISM: Escherichia coli

<400> SEQUENCE: 18

Leu Arg Tyr Gly Arg Ala Tyr His Leu Ala Pro Val Leu Gln
1               5                   10

<210> SEQ ID NO 19
<211> LENGTH: 4824
<212> TYPE: DNA
<213> ORGANISM: Artificial Sequence
<220> FEATURE:
<223> OTHER INFORMATION: includes sequences from Helicobacter pylori,
      Salmonella typhimurium, and Escherichia coli
<221> NAME/KEY: CDS
<222> LOCATION: (3893)...(3934)
<221> NAME/KEY: CDS
<222> LOCATION: (3938)...(4027)
<221> NAME/KEY: CDS
<222> LOCATION: (4031)...(4285)
<221> NAME/KEY: CDS
<222> LOCATION: (4289)...(4300)
<221> NAME/KEY: CDS
<222> LOCATION: (4304)...(4408)
<221> NAME/KEY: CDS
<222> LOCATION: (4412)...(4471)
<221> NAME/KEY: CDS
<222> LOCATION: (4475)...(4588)
<221> NAME/KEY: CDS
<222> LOCATION: (4592)...(4669)
<221> NAME/KEY: CDS
<222> LOCATION: (4673)...(4711)
<221> NAME/KEY: CDS
```

<222> LOCATION: (4715)...(4774)
<221> NAME/KEY: CDS
<222> LOCATION: (4784)...(4824)

<400> SEQUENCE: 19

```
gaattctatt ccggaacttc gcgttataaa atgaatctga cgtacacagc aatttagata      60
ttaatcatcc acaggagaga tctccatgaa actcacccca aaagagttag ataagttgat     120
gctccactac gctggagaat tggctaaaaa acgcaaagaa aaaggcatta agcttaacta     180
tgtagaagca gtagctttga ttagtgccca tattatggaa gaagcgagag ctggtaaaaa     240
gactgcggct gaattgatgc aagaagggcg cactctttta aaaccagatg atgtgatgga     300
tggcgtggca agcatgatcc atgaagtggg tattgaagcg atgtttcctg atgggactaa     360
actcgtaacc gtgcataccc ctattgaggc caatggtaaa ttagttcctg gtgagttgtt     420
cttaaaaaat gaagacatca ctatcaacga aggcaaaaaa gccgttagcg tgaaagttaa     480
aaatgttggc gacagaccgg ttcaaatcgg ctcacacttc catttctttg aagtgaatag     540
atgcctagac tttgacagag aaaaaacttt cggtaaacgc ttagacattg cgagcgggac     600
agcggtaaga tttgagcctg cgaagaaaaa atccgtagaa ttgattgaca ttggcggtaa     660
cagaagaatc tttggattta acgcattggt tgatagacaa gcagacaacg aaagcaaaaa     720
aattgcttta cacagagcta aagagcgtgg ttttcatggc gctaaaagcg atgacaacta     780
tgtaaaaaca attaaggagt aagaaatgaa aaagattagc agaaagaat atgtttctat     840
gtatggtcct actacaggcg ataaagtgag attgggcgat acagacttga tcgctgaagt     900
agaacatgac tacaccattt atggcgaaga gcttaaattc ggtggcggta aaaaccctaag    960
agaaggcatg agccaatcta caacccctag caaagaagag ttggatttaa ttatcactaa    1020
cgctttaatc gtggattaca ccggtattta taaagcggat attggtatta agatggcaa     1080
aatcgctggc attggtaaag gcggtaacaa agacatgcaa gatggcgtta aaacaatct    1140
tagcgtaggt cctgctactg aagccttagc cggtgaaggt ttgatcgtaa cggctggtgg    1200
tattgacaca cacatccact tcatttcacc ccaacaaatc cctacagctt ttgcaagcgg    1260
tgtaacaacc atgattggtg gtggaaccgg tcctgctgat ggcactaatg cgactactat    1320
cactccaggc agaagaaatt taaaatggat gctcagagcg gctgaagaat attctatgaa    1380
tttaggtttc ttggctaaag gtaacgcttc taacgatgcg agcttagccg atcaaattga    1440
agccggtgcg attggctttg caattcacga agactgggc accactcctt ctgcaatcaa     1500
tcatgcgtta gatgttgcgg acaaatacga tgtgcaagtc gctatcgcca cagacacttt    1560
gaatgaagcc ggttgtgtag aagacactat ggctgctatt gctggacgca ctatgcacac    1620
tttccacact gaaggcgctg gcggcggaca cgctcctgat attattaaag tagccggtga    1680
acacaacatt cttcccgctt ccactaaccc caccatccct ttcaccgtga atacagaagc    1740
agagcacatg gacatgctta tggtgtgcca ccacttggat aaaagcatta agaagatgt    1800
tcagttcgct gattcaagga tccgccctca aaccattgcg gctgaagaca ctttgcatga    1860
catggggatt ttctcaatca ccagttctga ctctcaagcg atgggccgtg tgggtgaagt    1920
tatcactaga acttggcaaa cagctgacaa aaacaagaaa gaatttggcc gcttgaaga     1980
agaaaaaggc gataacgaca acttcaggat caaacgctac ttgtctaaat acaccattaa    2040
cccagcgatc gctcatggga ttagcgagta tgtaggttca gtagaagtgg gcaaagtggc    2100
tgacttggta ttgtggagtc cagcattctt tggcgtgaaa cccaacatga tcatcaaagg    2160
cggattcatt gcgttaagcc aaatgggcga tgcgaacgct tctatcccta ccccacaacc    2220
```

-continued

```
ggtttattac agagaaatgt tcgctcatca tggtaaagct aaatacgatg caaacatcac    2280 tttttgtgtct caagcggctt atgacaaagg cattaaagaa gaattaggac ttgaaagaca   2340
agtgttgccg gtaaaaaatt gcagaaatat cactaaaaaa gacatgcaat tcaacgacac    2400
taccgctcac attgaagtca atcctgaaac ttaccatgtg ttcgtggatg caaagaagt     2460 aacttctaaa ccagccaata aagtgagctt ggcgcaactc tttagcattt tctaggattt    2520
tttaggagca acgctcctta gatccccggg aattggggat ccgctagccc gcctaatgag    2580
cgggcttttt tttctcgggc agcgttgggt cctggccacg ggtgcgcatg atcgtgctcc    2640
tgtcgttgag gacccggcta ggctggcggg gttgccttac tggttagcag aatgaatcac    2700
cgatacgcga gcgaacgtga agcgactgct gctgcaaaac gtctgcgacc tgagcaacaa    2760
catgaatggt cttcggtttc cgtgtttcgt aaagtctgga aacgcggaag tcagcgctct    2820
tccgcttcct cgctcactga ctcgctgcgc tcggtcgttc ggctgcggcg agcggtatca    2880
gctcactcaa aggcggtaat acggttatcc acagaatcag gggataacgc aggaaagaac    2940
atgtgagcaa aaggccagca aaaggccagg aaccgtaaaa aggccgcgtt gctggcgttt    3000
ttccataggc tccgcccccc tgacgagcat cacaaaaatc gacgctcaag tcagaggtgg    3060
cgaaacccga caggactata aagataccag gcgtttcccc ctggaagctc cctcgtgcgc    3120
tctcctgttc cgaccctgcc gcttaccgga tacctgtccg cctttctccc ttcgggaagc    3180
gtggcgcttt ctcaatgctc acgctgtagg tatctcagtt cggtgtaggt cgttcgctcc    3240
aagctgggct gtgtgcacga accccccgtt cagcccgacc gctgcgcctt atccggtaac    3300
tatcgtcttg agtccaaccc ggtaagacac gacttatcgc cactggcagc agccactggt    3360
aacaggatta gcagagcgag gtatgtaggc ggtgctacag agttcttgaa gtggtggcct    3420
aactacggct acactagaag gacagtattt ggtatctgcg ctctgctgaa gccagttacc    3480
ttcggaaaaa gagttggtag ctcttgatcc ggcaaacaaa ccaccgctgg tagcggtggt    3540
ttttttgttt gcaagcagca gattacgcgc agaaaaaaag gatctcaaga agatcctttg    3600
atcttttcta cggggtctga cgctcagtgg aacgaaaact cacgttaagg gattttggtc    3660
atgagattat caaaaaggat cttcacctag atccttttaa attaaaaatg aagttttaaa    3720
tcaatctaaa gtatatatga gtaaacttgg tctgacagtt accaatgctt aatcagtgag    3780
gcacctatct cagcgatctg tctatttcgt tcatccatag ttgcctgact ccccgtcgtg    3840
tagataacta cgatacggga gggcttacca tctggcccca gtgctgcaat ga tac cgc   3898
                                                           Tyr Arg
                                                             1 gag acc cac gct cac cgg ctc cag att tat cag caa taa acc agc cag      3946
Glu Thr His Ala His Arg Leu Gln Ile Tyr Gln Gln     Thr Ser Gln
  5                  10                   15 ccg gaa ggg ccg agc gca gaa gtg gtc ctg caa ctt tat ccg cct cca      3994
Pro Glu Gly Pro Ser Ala Glu Val Val Leu Gln Leu Tyr Pro Pro Pro
         20                  25                  30 tcc agt cta tta att gtt gcc ggg aag cta gag taa gta gtt cgc cag      4042
Ser Ser Leu Leu Ile Val Ala Gly Lys Leu Glu     Val Val Arg Gln
     35                  40                      45 tta ata gtt tgc gca acg ttg ttg cca ttg ctg cag gca tcg tgg tgt      4090
Leu Ile Val Cys Ala Thr Leu Leu Pro Leu Leu Gln Ala Ser Trp Cys
 50                  55                  60 cac gct cgt cgt ttg gta tgg ctt cat tca gct ccg gtt ccc aac gat      4138
His Ala Arg Arg Leu Val Trp Leu His Ser Ala Pro Val Pro Asn Asp
 65                  70                  75                  80
```

```
caa ggc gag tta cat gat ccc cca tgt tgt gca aaa aag cgg tta gct    4186
Gln Gly Glu Leu His Asp Pro Pro Cys Cys Ala Lys Lys Arg Leu Ala
                85                  90                  95 cct tcg gtc ctc cga tcg ttg tca gaa gta agt tgg ccg cag tgt tat    4234
Pro Ser Val Leu Arg Ser Leu Ser Glu Val Ser Trp Pro Gln Cys Tyr
            100                 105                 110 cac tca tgg tta tgg cag cac tgc ata att ctc tta ctg tca tgc cat    4282
His Ser Trp Leu Trp Gln His Cys Ile Ile Leu Leu Leu Ser Cys His
        115                 120                 125 ccg taa gat gct ttt ctg tga ctg gtg agt act caa cca agt cat tct    4330
Pro     Asp Ala Phe Leu     Leu Val Ser Thr Gln Pro Ser His Ser
    130                 135                 140 gag aat agt gta tgc ggc gac cga gtt gct ctt gcc cgg cgt caa cac    4378
Glu Asn Ser Val Cys Gly Asp Arg Val Ala Leu Ala Arg Arg Gln His
145                 150                 155 ggg ata ata ccg cgc cac ata gca gaa ctt taa aag tgc tca tca ttg    4426
Gly Ile Ile Pro Arg His Ile Ala Glu Leu     Lys Cys Ser Ser Leu
160                 165                 170 gaa aac gtt ctt cgg ggc gaa aac tct caa gga tct tac cgc tgt        4471
Glu Asn Val Leu Arg Gly Glu Asn Ser Gln Gly Ser Tyr Arg Cys
175                 180                 185 tga gat cca gtt cga tgt aac cca ctc gtg cac cca act gat ctt cag    4519
    Asp Pro Val Arg Cys Asn Pro Leu Val His Pro Thr Asp Leu Gln
        190                 195                 200 cat ctt tta ctt tca cca gcg ttt ctg ggt gag caa aaa cag gaa ggc    4567
His Leu Leu Leu Ser Pro Ala Phe Leu Gly Glu Gln Lys Gln Glu Gly
        205                 210                 215 aaa atg ccg caa aaa agg gaa taa ggg cga cac gga aat gtt gaa tac    4615
Lys Met Pro Gln Lys Arg Glu     Gly Arg His Gly Asn Val Glu Tyr
220                 225                 230 tca tac tct tcc ttt ttc aat att att gaa gca ttt atc agg gtt att    4663
Ser Tyr Ser Ser Phe Phe Asn Ile Ile Glu Ala Phe Ile Arg Val Ile
235                 240                 245                 250 gtc tca tga gcg gat aca tat ttg aat gta ttt aga aaa ata aac aaa    4711
Val Ser     Ala Asp Thr Tyr Leu Asn Val Phe Arg Lys Ile Asn Lys
                255                 260                 265 tag ggg ttc cgc gca cat ttc ccc gaa aag tgc cac ctg acg tct aag    4759
    Gly Phe Arg Ala His Phe Pro Glu Lys Cys His Leu Thr Ser Lys
                270                 275                 280 aaa cca tta tta tca tgacattaa cct ata aaa ata ggc gta tca cga ggc  4810
Lys Pro Leu Leu Ser           Pro Ile Lys Ile Gly Val Ser Arg Gly
                285                         290 cct ttc gtc ttc aa                                                 4824
Pro Phe Val Phe
295

<210> SEQ ID NO 20
<211> LENGTH: 14
<212> TYPE: PRT
<213> ORGANISM: Escherichia coli

<400> SEQUENCE: 20

Tyr Arg Glu Thr His Ala His Arg Leu Gln Ile Tyr Gln Gln
1               5                   10

<210> SEQ ID NO 21
<211> LENGTH: 30
<212> TYPE: PRT
<213> ORGANISM: Escherichia coli

<400> SEQUENCE: 21
```

```
Thr Ser Gln Pro Glu Gly Pro Ser Ala Glu Val Val Leu Gln Leu Tyr
 1               5                  10                  15
Pro Pro Pro Ser Ser Leu Leu Ile Val Ala Gly Lys Leu Glu
                 20                  25                  30
```

<210> SEQ ID NO 22
<211> LENGTH: 85
<212> TYPE: PRT
<213> ORGANISM: Escherichia coli

<400> SEQUENCE: 22

```
Val Val Arg Gln Leu Ile Val Cys Ala Thr Leu Leu Pro Leu Leu Gln
 1               5                  10                  15
Ala Ser Trp Cys His Ala Arg Arg Leu Val Trp Leu His Ser Ala Pro
                 20                  25                  30
Val Pro Asn Asp Gln Gly Glu Leu His Asp Pro Pro Cys Cys Ala Lys
                 35                  40                  45
Lys Arg Leu Ala Pro Ser Val Leu Arg Ser Leu Ser Glu Val Ser Trp
             50                  55                  60
Pro Gln Cys Tyr His Ser Trp Leu Trp Gln His Cys Ile Ile Leu Leu
65                   70                  75                  80
Leu Ser Cys His Pro
                 85
```

<210> SEQ ID NO 23
<211> LENGTH: 4
<212> TYPE: PRT
<213> ORGANISM: Escherichia coli

<400> SEQUENCE: 23

```
Asp Ala Phe Leu
 1
```

<210> SEQ ID NO 24
<211> LENGTH: 35
<212> TYPE: PRT
<213> ORGANISM: Escherichia coli

<400> SEQUENCE: 24

```
Leu Val Ser Thr Gln Pro Ser His Ser Glu Asn Ser Val Cys Gly Asp
 1               5                  10                  15
Arg Val Ala Leu Ala Arg Arg Gln His Gly Ile Ile Pro Arg His Ile
                 20                  25                  30
Ala Glu Leu
         35
```

<210> SEQ ID NO 25
<211> LENGTH: 20
<212> TYPE: PRT
<213> ORGANISM: Escherichia coli

<400> SEQUENCE: 25

```
Lys Cys Ser Ser Leu Glu Asn Val Leu Arg Gly Glu Asn Ser Gln Gly
 1               5                  10                  15
Ser Tyr Arg Cys
                 20
```

<210> SEQ ID NO 26
<211> LENGTH: 38
<212> TYPE: PRT
<213> ORGANISM: Escherichia coli

```
<400> SEQUENCE: 26

Asp Pro Val Arg Cys Asn Pro Leu Val His Pro Thr Asp Leu Gln His
 1               5                  10                  15

Leu Leu Leu Ser Pro Ala Phe Leu Gly Glu Gln Lys Gln Glu Gly Lys
            20                  25                  30

Met Pro Gln Lys Arg Glu
            35

<210> SEQ ID NO 27
<211> LENGTH: 26
<212> TYPE: PRT
<213> ORGANISM: Escherichia coli

<400> SEQUENCE: 27

Gly Arg His Gly Asn Val Glu Tyr Ser Tyr Ser Ser Phe Phe Asn Ile
 1               5                  10                  15

Ile Glu Ala Phe Ile Arg Val Ile Val Ser
            20                  25

<210> SEQ ID NO 28
<211> LENGTH: 13
<212> TYPE: PRT
<213> ORGANISM: Escherichia coli

<400> SEQUENCE: 28

Ala Asp Thr Tyr Leu Asn Val Phe Arg Lys Ile Asn Lys
 1               5                  10

<210> SEQ ID NO 29
<211> LENGTH: 20
<212> TYPE: PRT
<213> ORGANISM: Salmonella typhimurium

<400> SEQUENCE: 29

Gly Phe Arg Ala His Phe Pro Glu Lys Cys His Leu Thr Ser Lys Lys
 1               5                  10                  15

Pro Leu Leu Ser
            20

<210> SEQ ID NO 30
<211> LENGTH: 13
<212> TYPE: PRT
<213> ORGANISM: Salmonella typhimurium

<400> SEQUENCE: 30

Pro Ile Lys Ile Gly Val Ser Arg Gly Pro Phe Val Phe
 1               5                  10

<210> SEQ ID NO 31
<211> LENGTH: 31
<212> TYPE: DNA
<213> ORGANISM: Helicobacter pylori

<400> SEQUENCE: 31
tagggaattc tcatgaaact caccccaaaa g                              31

<210> SEQ ID NO 32
<211> LENGTH: 22
<212> TYPE: DNA
<213> ORGANISM: Helicobacter pylori

<400> SEQUENCE: 32
```
gccaacttag cttcctttcg gg                                           22

<210> SEQ ID NO 33
<211> LENGTH: 34
<212> TYPE: DNA
<213> ORGANISM: Helicobacter pylori

<400> SEQUENCE: 33
tctactgcag gatccaaaat gctaaagagt tgcg                              34

<210> SEQ ID NO 34
<211> LENGTH: 21
<212> TYPE: DNA
<213> ORGANISM: Salmonella typhimurium

<400> SEQUENCE: 34
tcaaatggta ccccttgctg a                                            21

<210> SEQ ID NO 35
<211> LENGTH: 20
<212> TYPE: DNA
<213> ORGANISM: Salmonella typhimurium

<400> SEQUENCE: 35
tattccggaa cttcgcgtta                                              20

<210> SEQ ID NO 36
<211> LENGTH: 23
<212> TYPE: DNA
<213> ORGANISM: Helicobacter pylori

<400> SEQUENCE: 36
tgtttcctga tgggactaaa ctc                                          23

<210> SEQ ID NO 37
<211> LENGTH: 22
<212> TYPE: DNA
<213> ORGANISM: Helicobacter pylori

<400> SEQUENCE: 37
accaggaact aatttaccat tg                                           22

<210> SEQ ID NO 38
<211> LENGTH: 21
<212> TYPE: DNA
<213> ORGANISM: Helicobacter pylori

<400> SEQUENCE: 38
ttgattgaca ttggcggtaa c                                            21

<210> SEQ ID NO 39
<211> LENGTH: 22
<212> TYPE: DNA
<213> ORGANISM: Helicobacter pylori

<400> SEQUENCE: 39
gttgtctgct tgtctatcaa cc                                           22

<210> SEQ ID NO 40
<211> LENGTH: 22
<212> TYPE: DNA
<213> ORGANISM: Helicobacter pylori -continued

```
<400> SEQUENCE: 40
ggtggcggta aaccctaag ag                                            22

<210> SEQ ID NO 41
<211> LENGTH: 22
<212> TYPE: DNA
<213> ORGANISM: Helicobacter pylori

<400> SEQUENCE: 41
ctttgctagg gttgttagat tg                                           22

<210> SEQ ID NO 42
<211> LENGTH: 22
<212> TYPE: DNA
<213> ORGANISM: Helicobacter pylori

<400> SEQUENCE: 42
aatccctaca gcttttgcaa gc                                           22

<210> SEQ ID NO 43
<211> LENGTH: 22
<212> TYPE: DNA
<213> ORGANISM: Helicobacter pylori

<400> SEQUENCE: 43
gtgccatcag caggaccggt tc                                           22

<210> SEQ ID NO 44
<211> LENGTH: 22
<212> TYPE: DNA
<213> ORGANISM: Helicobacter pylori

<400> SEQUENCE: 44
atcgccacag acactttgaa tg                                           22

<210> SEQ ID NO 45
<211> LENGTH: 22
<212> TYPE: DNA
<213> ORGANISM: Helicobacter pylori

<400> SEQUENCE: 45
tagcagccat agtgtcttct ac                                           22

<210> SEQ ID NO 46
<211> LENGTH: 22
<212> TYPE: DNA
<213> ORGANISM: Helicobacter pylori

<400> SEQUENCE: 46
tgaagacact ttgcatgaca tg                                           22

<210> SEQ ID NO 47
<211> LENGTH: 22
<212> TYPE: DNA
<213> ORGANISM: Helicobacter pylori

<400> SEQUENCE: 47
tgagagtcag aactggtgat tg                                           22

<210> SEQ ID NO 48
<211> LENGTH: 22
<212> TYPE: DNA
<213> ORGANISM: Helicobacter pylori
```

```
<400> SEQUENCE: 48
catgatcatc aaaggcggat tc                                         22

<210> SEQ ID NO 49
<211> LENGTH: 23
<212> TYPE: DNA
<213> ORGANISM: Helicobacter pylori

<400> SEQUENCE: 49
gaagcgttcg catcgcccat ttg                                        23

<210> SEQ ID NO 50
<211> LENGTH: 22
<212> TYPE: DNA
<213> ORGANISM: Helicobacter pylori

<400> SEQUENCE: 50
tcgtggatgg caaagaagta ac                                         22

<210> SEQ ID NO 51
<211> LENGTH: 20
<212> TYPE: DNA
<213> ORGANISM: Helicobacter pylori

<400> SEQUENCE: 51
gcgccaagct cactttattg                                            20

<210> SEQ ID NO 52
<211> LENGTH: 22
<212> TYPE: DNA
<213> ORGANISM: Salmonella typhimurium

<400> SEQUENCE: 52
caacgacagg agcacgatca tg                                         22
```

What is claimed is:

1. A method of inducing an immune response against Helicobacter in a mammal, said method comprising the steps of:

mucosally administering to said mammal an attenuated Salmonella vector comprising a nucleic acid molecule encoding a Helicobacter antigen, and parenterally administering to said mammal a Helicobacter antigen.

2. The method of claim 1, wherein said attenuated Salmonella vector is administered orally to said mammal.

3. The method of claim 1, wherein said Helicobacter antigen is a urease, a urease subunit, or an immunogenic fragment thereof.

4. The method of claim 1, wherein said mammal is at risk of developing, but does not have, a Helicobacter infection.

5. The method of claim 1, wherein said mammal has a Helicobacter infection.

6. The method of claim 1, wherein said parenteral administration of said Helicobacter antigen further includes parenteral administration of an adjuvant.

7. The method of claim 6, wherein said adjuvant is an aluminum compound.

8. The method of claim 7, wherein said aluminum compound is alum.

9. The method of claim 1, wherein said attenuated Salmonella vector is a *Salmonella typhi* vector.

10. The method of claim 9, wherein said *Salmonella typhi* vector is CVD908-htrA or CVD908.

11. The method of claim 1, wherein the attenuated Salmonella vector is a *Salmonella typhimurium* vector.

12. The method of claim 11, wherein said *Salmonella typhimurium* vector is BRD509 or BRD807.

13. The method of claim 1, wherein said attenuated Salmonella vector further comprises an htrA promoter.

14. The method of claim 1, wherein said attenuated Salmonella vector further comprises a nirB promoter.

15. The method of claim 1, wherein said mucosal administration primes an immune response to an antigen and said parenteral administration boosts an immune response to said antigen.

* * * * *